(12) United States Patent
Chen et al.

(10) Patent No.: US 9,133,105 B2
(45) Date of Patent: Sep. 15, 2015

(54) TRANSCRIPTION FACTOR MODULATORS

(71) Applicant: C & C BIOPHARMA, LLC, Los Angeles, CA (US)

(72) Inventors: Lin Chen, La Canada Flintridge, CA (US); Xiaojiang Chen, South Pasadena, CA (US); Yongqing Wu, Irvine, CA (US); Dahai Gai, La Crescenta, CA (US)

(73) Assignee: C&C BIOPHARMA, LLC, Los Angeles, CA (US)

( * ) Notice: Subject to any disclaimer, the term of this patent is extended or adjusted under 35 U.S.C. 154(b) by 0 days.

(21) Appl. No.: 13/843,612

(22) Filed: Mar. 15, 2013

(65) Prior Publication Data

US 2014/0256775 A1    Sep. 11, 2014

Related U.S. Application Data

(60) Provisional application No. 61/773,798, filed on Mar. 6, 2013.

(51) Int. Cl.
| | | |
|---|---|---|
| C07C 237/22 | (2006.01) | |
| C07D 215/40 | (2006.01) | |
| C07D 213/75 | (2006.01) | |
| C07C 237/52 | (2006.01) | |
| C07D 213/40 | (2006.01) | |
| C07C 233/42 | (2006.01) | |

(52) U.S. Cl.
CPC ............ *C07C 237/52* (2013.01); *C07C 233/42* (2013.01); *C07D 213/40* (2013.01); *C07D 213/75* (2013.01)

(58) Field of Classification Search
USPC ........... 514/352, 357, 616; 546/337, 157, 308
See application file for complete search history.

(56) References Cited

U.S. PATENT DOCUMENTS

| 5,369,108 A | 11/1994 | Breslow et al. | |
|---|---|---|---|
| 5,700,811 A | 12/1997 | Breslow | |
| 2006/0160201 A1 | 7/2006 | Chen | |
| 2011/0275674 A1 | 11/2011 | Chen | |
| 2012/0094971 A1* | 4/2012 | Rusche et al. | ........... 514/210.01 |

FOREIGN PATENT DOCUMENTS

| WO | WO2007058927 | 5/2007 |
|---|---|---|
| WO | WO2010028193 | 3/2011 |

OTHER PUBLICATIONS

Nimanthi Jayathilaka, et al., "Inhibition of the function of class IIa HDACs by blocking their interaction with MEF2" Nucleic Acids Research, Mar. 6, 2012, pp. 5378-5388, vol. 40, No. 12, Oxford University Press, United Kingdom, Published Online.

Jurate Savickiene, et al. "The novel histone deacetylase inhibitor BML-210 exerts growth inhibitiory, proapoptotic and differentiation stimulating effects on the human leukemia cell lines"; European Journal of Pharmacology, vol. 549, pp. 9-18, Aug. 15, 2006. Elsevier/Science Direct, published online.

V.V. Borutinskaite, et. al., "Apoptotic effects of the novel histone deacetylase inhibitor BML-210 on HeLa cells" Biologija, 2008, pp. 217-220, vol. 54, No. 3 Published online by Lithuanian Academy of Sciences, Vilnius, Lithuania.

Marielle Paris, et. al., "Histone Deacetylase Inhibitors: From Bench to Clinic"; Journal of Medicinal Chemistry, Mar. 27, 2008, pp. 1505-1529, vol. 51, No. 6, Published by the American Chemical Society, United States.

Andrea Clocchiatti, et al., "Beside the MEF2 axis: Unconventional functions of HDAC4", Cellular Signalling, Oct. 11, 2012, pp. 269-276, vol. 25, No. 1.

Zhenhua Lin, et al., "Combination of Proteasome and HDAC Inhibitors for Uterine Cervical Cancer Treatment", Clinical Cancer Research, Jan. 15, 2009, pp. 570-577, vol. 15, No. 2.

Veronicka V. Borutinskaite. et. al., "Retinoic Acid and Histone Deacetylase Inhibitor BML-210 Inhibit Proliferation of Human Cervical Cancer HeLa Cells" Annals New York Academy of Sciences. 2006, pp. 346-355, United States.

Elizabeth Thomas, et al. "The HDAC inhibitor 4b ameliorates the disease phenotype and transcriptional abnormalities in Huntington's disease transgenic mice", Proceedings of the National Academy of Sciences of the United States of America, Oct. 7, 2008, pp. 15564-15569, vol. 105, No. 40. Published online in the United States.

United States Patent and Trademark Office, International Search Report and Written Opinion dated Aug. 12, 2014 for PCT/US2014/021452.

Matthew J. Potthoff, et al., "MEF2: a central regulator of diverse developmental programs," Development 134, 4131-4140 (2007).

Audrey H. Wang, et al., "Histone Deacetylase 4 Possesses Intrinsic Nuclear Import and Export Signals," Mol. Cell. Biol. Sep. 2001, p. 5992-6005, vol. 21, No. 17.

James E. Bradner, et al., "Chemical Phylogenetics of Histone Deacetylases," Nat. Chem. Biol. Mar. 2010; 6 (3):238-243.

Lin Wu, et al., "Multidrug-resistant Phenotype of Disease-oriented Panels of Human Tumor Cell Lines Used for Anticancer Drug Screening," Cancer Res. 1992, 52:3029-3034.

Jianrong Lu, et al., "Regulation of Skeletal Myogenesis by Association of the MEF2 Transcription Factor with Class II Histone Deacetylases," Mol. Cell 6:233-244 (2000).

Aidong Han, et al., "Mechanism of Recruitment of Class II Histone Deacetylases by Myocyte Enhancer Factor-2," J. Mol. Biol. 345:91-102 (2005).

Aidong Han, et al., "Sequence-specific recruitment of transcriptional co-repressor Cabin1 by myocyte enhancer factor-2," Nature 422:730-734 (2003).

\* cited by examiner

*Primary Examiner* — Shirley V Gembeh

(74) *Attorney, Agent, or Firm* — Perkins Coie LLP; Courtney Prochnow

(57) ABSTRACT

The present disclosure provides novel compounds capable of functioning as transcription factor modulators, as well as compositions, pharmaceutical formulations, and kits. Also provided are methods of treating a condition regulatable by a transcription factor and/or cofactor using the compounds, compositions, pharmaceutical formulations, and kits provided herein.

3 Claims, 2 Drawing Sheets

US 9,133,105 B2

TRANSCRIPTION FACTOR MODULATORS

PRIORITY CLAIM

This application claims priority to U.S. Provisional Patent Application Ser. No. 61/773,798, filed Mar. 6, 2013, which is incorporated herein by reference in its entirety, as if fully set forth herein.

BACKGROUND

Alterations of epigenetic regulation are a characteristic of many diseases. The myocyte enhancer factor 2 (MEF2) transcription factor plays central roles in the transmission of extracellular signals to the genome and in the activation of the genetic programs that control cell differentiation, proliferation, morphogenesis, survival and apoptosis of a wide range of cell types (Potthoff et al., 2007). The spectrum of genes activated by MEF2 in different cell types depends on extracellular signaling and on cofactor interactions that modulate MEF2 activity. To drive the expression of MEF2 target genes, MEF2 relies on the recruitment of and cooperation with a number of transcription factors including, but not limited to, calcineurin binding protein 1, E1A binding protein P300, CREB binding protein, extracellular signal-regulated kinase 5, myoblast differentiation protein, Smad protein, nuclear factor of activated T cell, myocardin, and positive transcription elongation factor b.

Histone deacetylases (HDACs) are a major class of epigenetic regulators of diverse cellular processes. This family of enzymes can be phylogenetically divided into four classes: class I (HDAC1, 2, 3 and 8), class II (HDAC4, 5, 7, 9, 6 and 10) and class IV (HDAC 11), while class III (sirtuins, Sirt1-Sirt7) represents a structurally and functionally distinct family of HDAC enzymes. Class II HDACs can be further divided into class IIa (HDAC 4, 5, 7, and 9) and class IIb (HDAC 6 and 10). Recent studies show that MEF2 forms an intimate partnership with class IIa histone deacetylases (HDACx), which together function as a point of convergence of multiple epigenetic regulatory mechanisms.

Class IIa HDACs contain a unique regulatory domain, which is N-terminal to the catalytic domain and absent in other HDAC members. This regulatory HDAC domain mediates interactions with the Myocyte Enhancer Factor-2 (MEF2A-D) transcription factor proteins. Class IIa HDACs do not bind to DNA but depend on their interaction with the sequence-specific transcription factor MEF2 for genomic targeting (Wang et al., 2001; Han et al., 2005). This interaction is mediated by a short amphipathic helix conserved in the N-terminal regulatory domain of class IIa HDACs. Crystallography analyses and in vitro biochemical studies reveal that the amphipathic helix binds to a highly conserved hydrophobic groove on the MADS-box/MEF2 domain of MEF2 (Han et al., 2005; Han et al., 2003).

SUMMARY

One aspect of the present disclosure relates to compounds comprising a structure selected from the group consisting of Structure I, Structure II, Structure IIIA, Structure IIIB, Structure IIIC, Structure IVA, Structure IVB, Structure IVC, Structure IVD, Structure VA, Structure VB, Structure VC, Structure VD, Structure VE, Structure VI, Structure VIIA, Structure VIIB, Structure VIIC, Structure VIID, Structure VIIE, Structure VIII, and Structure IX, including pharmaceutically acceptable solvates, pharmaceutically acceptable prodrugs, pharmaceutically acceptable salts and pharmaceutically acceptable stereoisomers thereof. Other aspects relate to compositions, pharmaceutical formulations, and kits comprising the compounds disclosed herein.

Another aspect of the present disclosure relates to a method of treating a subject for a condition regulatable by a transcription factor and/or cofactor by administering to the subject one or more of the compounds, compositions, or pharmaceutical formulations provided herein.

Another aspect of the present disclosure relates to the use of one or more of the compounds, compositions, or pharmaceutical formulations provided herein in the manufacture of a medicament for the treatment of a condition regulatable by a transcription factor and/or cofactor.

Another aspect of the present disclosure relates to kits comprising one or more of the compounds, compositions, or pharmaceutical formulations provided herein.

DETAILED DESCRIPTION

Figure 1:
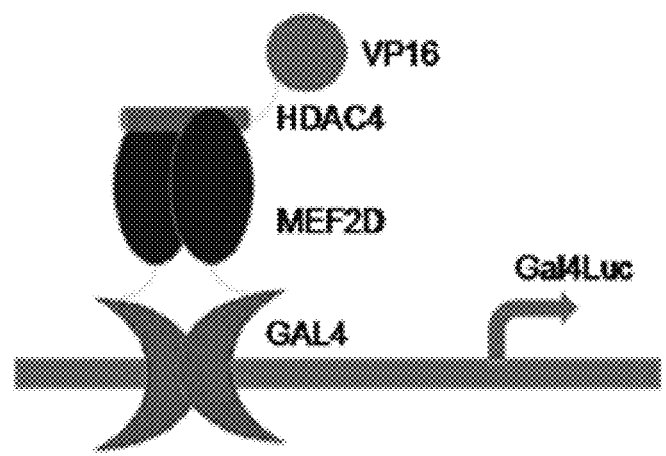
FIG. 1—An illustration of the mammalian two-hybrid system used for drug screening. The MEF2D (ovals) was fused with GAL4-DNA binding domain (half moons). The MEF2-binding motif of HDAC4 (amino acid residues 155-220, short rectangle) was fused with VP-16 (circle). When the GAL4-MEF2D and HDAC4-VP16 protein complex binds the DNA promoter site, expression of luciferase protein was induced in the HeLa cell as a reporter signal.

Most of the currently known small molecule compounds that alter epigenetic regulations target the active site of the HDACs of class I, II, and IV (Bradner et. al., 2010). Class IIa HDAC proteins do not respond to most of these existing HDAC inhibitors (Bradner et. al., 2010). Moreover, the broad inhibition of HDACs using active site inhibitors leads to complex cellular responses, which may explain some of the undesired side effects of these drugs in clinical applications.

Therefore, there is a need for developing small molecules that specifically target a particular HDAC or subset of HDACs to exploit the full therapeutic potential of HDAC inhibition in a wide range of diseases. Additionally, there is a need for developing small molecules that specifically target and inhibit class IIa HDACs that do not respond to existing HDAC inhibitors. Lastly, there is a need for developing small molecules that regulate MEF2 interactions as a new therapeutic target for treating diseases related to dysfunctional epigenetic regulation.

I. Compounds

One aspect of the present disclosure relates to compounds comprising a structure selected from the group consisting of Structure I, Structure II, Structure IIIA, Structure IIIB, Structure IIIC, Structure IVA, Structure IVB, Structure IVC, Structure IVD, Structure VA, Structure VB, Structure VC, Structure VD, Structure VE, Structure VI, Structure VIIA, Structure VIIB, Structure VIIC, Structure VIID, Structure VIIE, Structure VIII, and Structure IX, including pharmaceutically acceptable solvates, pharmaceutically acceptable prodrugs, pharmaceutically acceptable salts and pharmaceutically acceptable stereoisomers thereof. In certain embodiments, the compounds provided herein are transcription factor modulators.

Structure I

In certain embodiments, the compounds provided herein comprise a structure of Structure I:

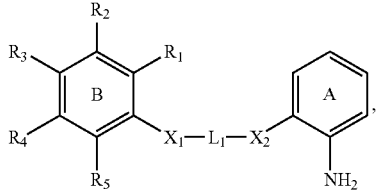

Structure I including pharmaceutically acceptable solvates, pharmaceutically acceptable prodrugs, pharmaceutically acceptable salts and pharmaceutically acceptable stereoisomers thereof, wherein:

A and B rings are each independently selected from the group consisting of phenyl, pyridyl and N-alkylated pyridyl rings;

$R_1$-$R_5$ are each independently selected from the group consisting of hydrogen, halogen, alkyl, OH, alkoxy, haloalkyl, aryl, heteroaryl, aryl carbonyl, and amino, wherein at least one or two of $R_1$-$R_5$ are not hydrogen.

$X_1$ and $X_2$ are independently selected from —NHC(=O)— or —C(=O)—NH—; and $L_1$ is —(CH$_2$)$_n$—, where n is 4, 5, 6, 7, or 8, where one or more —CH$_2$— moieties are optionally replaced with one or more substituents selected from the group consisting of —O—, —S—, —C(=O)—, —S(=O)—, —S(=O)$_2$—, —NH—C(=O)—, —C(=O)—NH—, —NR— (wherein R is hydrogen, alkyl or aryl), —C≡C—, carbon-carbon triple bond, phenylene (e.g. 1,4-phenylene) and cyclohexylene (e.g. 1,4-cyclohexylene). In certain of these embodiments, the compounds are transcription factor modulators.

In certain embodiments, $L_1$ is —(CH$_2$)$_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

In certain embodiments, A ring is a phenyl ring, and B ring is a pyridyl ring or N-alkylated pyridyl ring.

In certain embodiments, both A and B rings are phenyl rings.

In certain embodiments, A ring is a pyridyl ring, and B ring is a phenyl ring or N-alkylated pyridyl ring.

In certain embodiments, both A and B rings are pyridyl rings.

In certain embodiments, A ring is an N-alkylated pyridyl ring, and B ring is a phenyl ring or pyridyl ring.

In certain embodiments, both A and B rings are N-alkylated pyridyl rings.

In certain embodiments, $R_4$ and/or $R_5$ are/is haloalkyl (e.g. trifluoromethyl).

In certain embodiments, $R_4$ and/or $R_5$ are/is halogen (e.g. Br).

In certain embodiments, when $R_4$ is Br, at least one of $R_1$, $R_2$, $R_3$, and $R_5$ is not H In certain embodiments, one of $R_4$ and $R_5$ is haloalkyl (e.g. trifluoromethyl), and the other is halogen (e.g. Br).

In certain embodiments, $R_3$, $R_4$ and/or $R_5$ are/is haloalkyl (e.g. trifluoromethyl).

In certain embodiments, $R_3$, $R_4$ and/or $R_5$ are/is halogen (e.g. Br).

In certain embodiments, $R_3$, $R_4$ and/or $R_5$ are/is hydroxyl.

In certain embodiments, $R_3$, $R_4$ and/or $R_5$ are selected from the group consisting of halogen (e.g. F, Cl, Br, and I), alkyl (e.g. CH$_3$, C$_2$H$_5$), OH, alkoxy (e.g. OCH$_3$, and OCH$_2$CH$_3$), haloalkyl (e.g. CF$_3$), aryl (e.g. phenyl), heteroaryl (e.g. pyridyl), aryl carbonyl (e.g. phenylcarbonyl), and amino (e.g. NH$_2$).

Structure II

In certain embodiments, the compounds provided herein comprise a structure of Structure II:

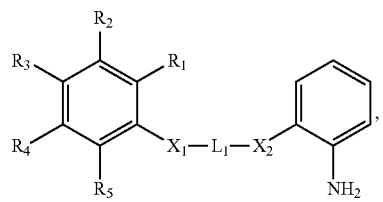

Structure II including pharmaceutically acceptable solvates, pharmaceutically acceptable prodrugs, pharmaceutically acceptable salts and pharmaceutically acceptable stereoisomers thereof, wherein $R_1$-$R_5$, $X_1$, $X_2$, and $L_1$ are defined the same as above. In certain of these embodiments, the compounds are transcription factor modulators.

In certain embodiments, $R_3$, $R_4$ and/or $R_5$ are/is haloalkyl (e.g. trifluoromethyl).

In certain embodiments, $R_3$, $R_4$ and/or $R_5$ are/is halogen (e.g. Br).

In certain embodiments, $R_3$, $R_4$ and/or $R_5$ are/is hydroxyl.

In certain embodiments, $R_3$, $R_4$ and/or $R_5$ are selected from the group consisting of halogen (e.g. F, Cl, Br, and I), alkyl (e.g. CH$_3$, C$_2$H$_5$), OH, alkoxy (e.g. OCH$_3$, and OCH$_2$CH$_3$), haloalkyl (e.g. CF$_3$), aryl (e.g. phenyl), heteroaryl (e.g. pyridyl), aryl carbonyl (e.g. phenylcarbonyl), and amino (e.g. NH$_2$).

In certain embodiments, $L_1$ is —(CH$_2$)$_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Structure III

In certain embodiments, the compounds provided herein comprise a structure selected from the group consisting of Structures IIIA-IIIC:

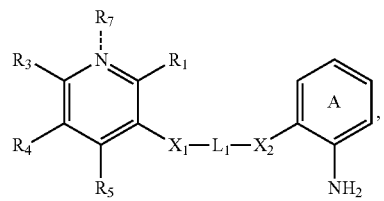

Structure IIIA

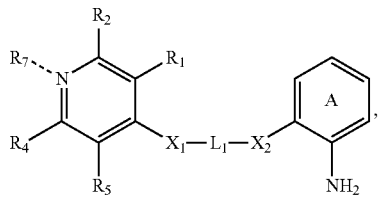

Structure IIIB

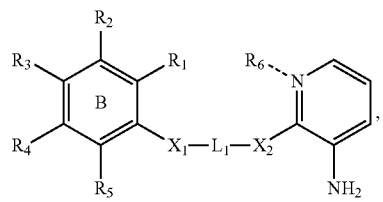

Structure IVA

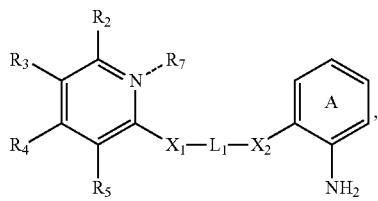

Structure IIIC

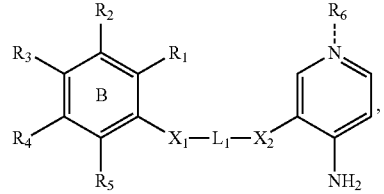

Structure IVB

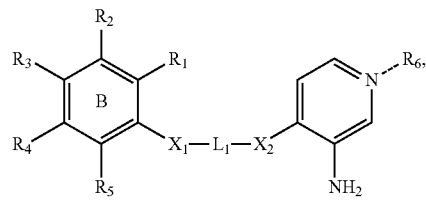

Structure IVC

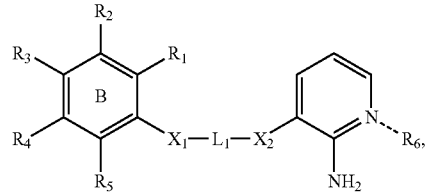

Structure IVD including pharmaceutically acceptable solvates, pharmaceutically acceptable prodrugs, pharmaceutically acceptable salts and pharmaceutically acceptable stereoisomers thereof, wherein:

A ring, $R_1$-$R_5$, $X_1$, $X_2$, and $L_1$ are defined the same as above; and $R_7$ is alkyl group having 1-3 carbon atoms (e.g. methyl). In certain of these embodiments, the compounds are transcription factor modulators.

In certain embodiments, the N-alkylated pyridine ring of Structures IIIA-IIIC may be positively charged and form a salt with one or more suitable counterions (e.g., without limitations, anions derived from pharmaceutically acceptable acids described herein, e.g. acetate, fluoroacetate or other carboxylate).

In certain embodiments, $R_3$, $R_4$ and/or $R_5$ are/is haloalkyl (e.g. trifluoromethyl).

In certain embodiments, $R_3$, $R_4$ and/or $R_5$ are/is halogen (e.g. Br).

In certain embodiments, $R_3$, $R_4$ and/or $R_5$ are/is hydroxyl.

In certain embodiments, $R_3$, $R_4$ and/or $R_5$ are selected from the group consisting of halogen (e.g. F, Cl, Br, and I), alkyl (e.g. $CH_3$, $C_2H_5$), OH, alkoxy (e.g. $OCH_3$, and $OCH_2CH_3$), haloalkyl (e.g. $CF_3$), aryl (e.g. phenyl), heteroaryl (e.g. pyridyl), aryl carbonyl (e.g. phenylcarbonyl), and amino (e.g. $NH_2$).

In certain embodiments, one of $R_4$ and $R_5$ is haloalkyl (e.g. trifluoromethyl), and the other is halogen (e.g. Br).

In certain embodiments, A ring is a phenyl ring.

In certain embodiments, A ring is a pyridyl ring.

In certain embodiments, A ring is an N-alkylated pyridyl ring.

In certain embodiments, $L_1$ is —$(CH_2)_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Structure IV

In certain embodiments, the compounds provided herein comprise a structure selected from the group consisting of Structures IVA-IVD:

including pharmaceutically acceptable solvates, pharmaceutically acceptable prodrugs, pharmaceutically acceptable salts and pharmaceutically acceptable stereoisomers thereof, wherein:

B ring, $R_1$-$R_5$, $X_1$, $X_2$, and $L_1$ are defined the same as above; and $R_6$ is alkyl group having 1-3 carbon atoms (e.g. methyl). In certain of these embodiments, the compounds are transcription factor modulators.

In certain embodiments, the N-alkylated pyridine ring of Structures IVA-IVD may be positively charged and form a salt with one or more suitable counterions (e.g., without limitations, anions derived from pharmaceutically acceptable acids described herein, acetate, fluoroacetate or other carboxylate).

In certain embodiments, $R_3$, $R_4$ and/or $R_5$ are/is haloalkyl (e.g. trifluoromethyl).

In certain embodiments, $R_3$, $R_4$ and/or $R_5$ are/is halogen (e.g. Br).

In certain embodiments, $R_3$, $R_4$ and/or $R_5$ are selected from the group consisting of halogen (e.g. F, Cl, Br, and I), alkyl (e.g. $CH_3$, $C_2H_5$), OH, alkoxy (e.g. $OCH_3$, and $OCH_2CH_3$), haloalkyl (e.g. $CF_3$), aryl (e.g. phenyl), heteroaryl (e.g. pyridyl), aryl carbonyl (e.g. phenylcarbonyl), and amino (e.g. $NH_2$).

In certain embodiments, one of $R_4$ and $R_5$ is haloalkyl (e.g. trifluoromethyl), and the other is halogen (e.g. Br).

In certain embodiments, B ring is a phenyl ring.

In certain embodiments, B ring is a pyridyl ring.

In certain embodiments, B ring is an N-alkylated pyridyl ring.

In certain embodiments, $L_1$ is —$(CH_2)_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Structure V

In certain embodiments, the compounds provided herein comprise a structure selected from the group consisting of Structures VA-VE:

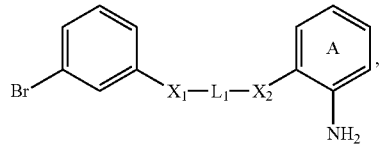
Structure VA

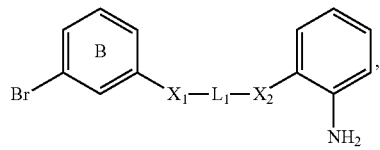
Structure VB

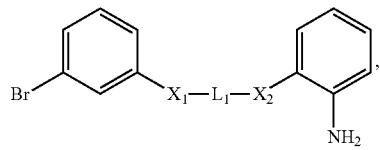
Structure VC

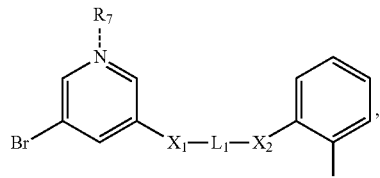
Structure VD

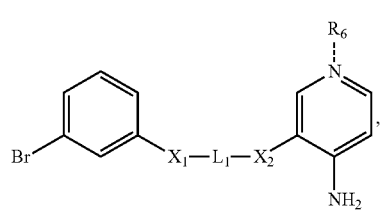
Structure VE including pharmaceutically acceptable solvates, pharmaceutically acceptable prodrugs, pharmaceutically acceptable salts and pharmaceutically acceptable stereoisomers thereof, wherein A ring, B ring, $R_1$-$R_7$, $X_1$, $X_2$, and $L_1$ are defined the same as above. In certain of these embodiments, the compounds are transcription factor modulators.

In certain embodiments, the N-alkylated pyridine ring of Structures VA-VE may be positively charged and form a salt with one or more suitable counterions (e.g., without limitations, anions derived from pharmaceutically acceptable acids described herein, e.g. acetate, fluoroacetate or other carboxylate).

In certain embodiments, $L_1$ is —$(CH_2)_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Structure VI

In certain embodiments, the compounds provided herein comprise a structure of Structure VI:

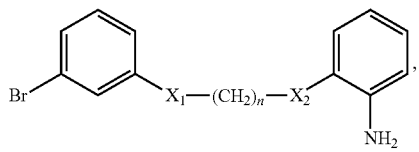
Structure VI including pharmaceutically acceptable solvates, pharmaceutically acceptable prodrugs, pharmaceutically acceptable salts and pharmaceutically acceptable stereoisomers thereof, wherein n, $X_1$, and $X_2$ are defined the same as above. In certain of these embodiments, the compounds are transcription factor modulators.

In certain embodiments, n is 4, 5, 6, 7, or 8.

In certain embodiments, —$X_1$—$(CH_2)_n$—$X_2$— is —NHC(=O)—$(CH_2)_n$—C(=O)NH—.

In certain embodiments, —$X_1$—$(CH_2)_n$—$X_2$— is —C(=O)—NH—$(CH_2)_n$—C(=O)NH—.

Structure VII

In certain embodiments, the compounds provided herein comprise a structure selected from the group consisting of Structures VIIA-VIIE:

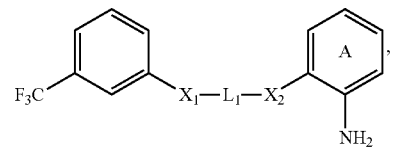
Structure VIIA

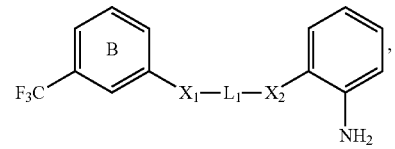
Structure VIIB

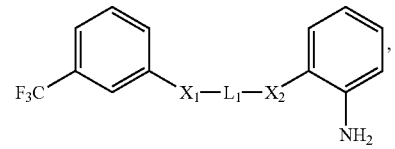
Structure VIIC

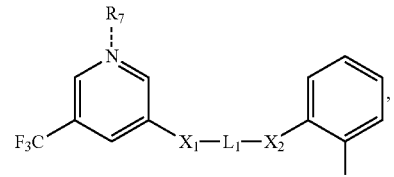
Structure VIID

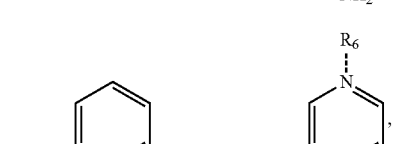
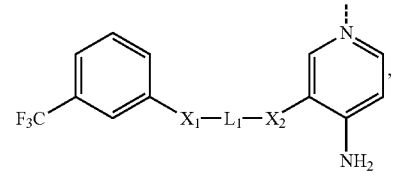
Structure VIIE including pharmaceutically acceptable solvates, pharmaceutically acceptable prodrugs, pharmaceutically acceptable salts and pharmaceutically acceptable stereoisomers thereof, wherein A ring, B ring, $R_1$-$R_7$, $X_1$, $X_2$, and $L_1$ are defined the same as above. In certain of these embodiments, the compounds are transcription factor modulators.

In certain embodiments, the N-alkylated pyridine ring of Structures VIIA-VIIE may be positively charged and form a salt with one or more suitable counterions (e.g., without limitations, anions derived from pharmaceutically acceptable acids described herein, e.g. acetate, fluoroacetate or other carboxylate).

In certain embodiments, $L_1$ is —$(CH_2)_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Structure VIII

In certain embodiments, the compounds provided herein comprise a structure of Structure VIII:

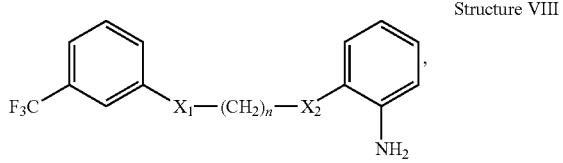

Structure VIII including pharmaceutically acceptable solvates, pharmaceutically acceptable prodrugs, pharmaceutically acceptable salts and pharmaceutically acceptable stereoisomers thereof, wherein n, $X_1$, and $X_2$ are defined the same as above. In certain of these embodiments, the compounds are transcription factor modulators.

In certain embodiments, n is 4, 5, 6, 7, or 8.

In certain embodiments, —$X_1$—$(CH_2)_n$—$X_2$— is —NHC(=O)—$(CH_2)_n$—C(=O)NH—.

In certain embodiments, —$X_1$—$(CH_2)_n$—$X_2$— is —C(=O)—NH—$(CH_2)_n$—C(=O)NH—.

Structure IX

In certain embodiments, the compounds provided herein comprise a structure of Structure IX:

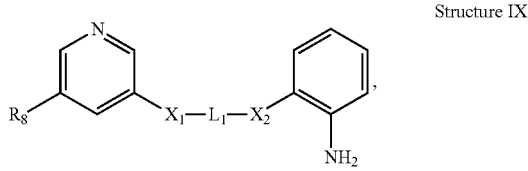

Structure IX including pharmaceutically acceptable solvates, pharmaceutically acceptable prodrugs, pharmaceutically acceptable salts and pharmaceutically acceptable stereoisomers thereof, wherein:

$X_1$, $X_2$ and $L_1$ are defined the same as above; and $R_8$ is selected from the group consisting of halogen (e.g. F, Cl, Br, and I), alkyl (e.g. $CH_3$, $C_2H_5$), OH, alkoxy (e.g. $OCH_3$, and $OCH_2CH_3$), haloalkyl (e.g. $CF_3$), aryl (e.g. phenyl), heteroaryl (e.g. pyridyl), aryl carbonyl (e.g. phenylcarbonyl), and amino (e.g. $NH_2$). In certain of these embodiments, the compounds are transcription factor modulators.

In certain embodiments, $L_1$ is —$(CH_2)_n$—, where n is 4, 5, 6, 7, or 8.

In certain embodiments, —$X_1$-$L_1$-$X_2$— is —NHC(=O)-$L_1$-C(=O)NH—.

In certain embodiments, —$X_1$-$L_1$-$X_2$— is —C(=O)—NH-$L_1$-C(=O)NH—.

Compounds CC Nos. 1~20

In certain embodiments, the compounds provided herein are selected from the group consisting of CC Nos. 1~20 listed in Table 1 below, including pharmaceutically acceptable solvates, pharmaceutically acceptable prodrugs, pharmaceutically acceptable salts and pharmaceutically acceptable stereoisomers thereof.

TABLE 1

| Structures of CC Nos. 1-20 | |
|---|---|
| CC No. | Structure |
| 1. | 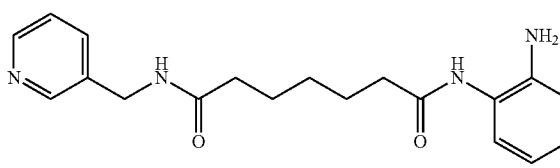 |
| 2. | 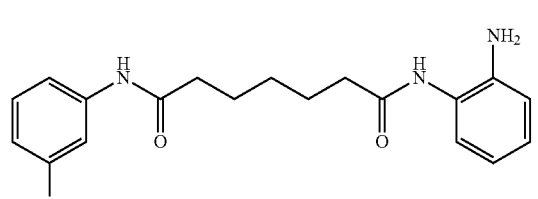 |
| 3. | 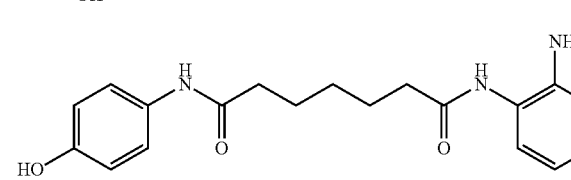 |

TABLE 1-continued

Structures of CC Nos. 1-20

| CC No. | Structure |
|---|---|
| 4. | 3-bromophenyl-NH-C(O)-(CH2)4-C(O)-NH-(4-aminopyridin-3-yl) |
| 5. | 4-bromophenyl-C(O)-NH-(CH2)4-C(O)-NH-(2-aminophenyl) |
| 6. | 2-bromophenyl-NH-C(O)-(CH2)4-C(O)-NH-(2-aminophenyl) |
| 7. | 5-bromopyridin-3-yl-NH-C(O)-(CH2)4-C(O)-NH-(2-aminophenyl) |
| 8. | 5-phenylpyridin-3-yl-NH-C(O)-(CH2)4-C(O)-NH-(2-aminophenyl) |
| 9. | 5-(pyridin-3-yl)pyridin-3-yl-NH-C(O)-(CH2)4-C(O)-NH-(2-aminophenyl) |
| 10. | 5-ethoxypyridin-3-yl-NH-C(O)-(CH2)4-C(O)-NH-(2-aminophenyl) |
| 11. | 5-hydroxypyridin-3-yl-NH-C(O)-(CH2)4-C(O)-NH-(2-aminophenyl) |
| 12. | 5-fluoropyridin-3-yl-NH-C(O)-(CH2)4-C(O)-NH-(2-aminophenyl) |

TABLE 1-continued
Structures of CC Nos. 1-20
| CC No. | Structure |
|---|---|
| 13. | 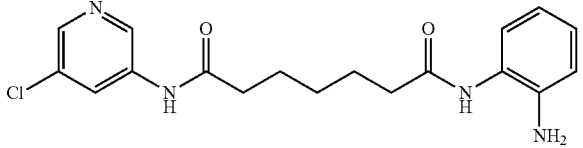 [SMILES: Nc1ccccc1NC(=O)CCCCCC(=O)Nc1cncc(Cl)c1] |
| 14. | 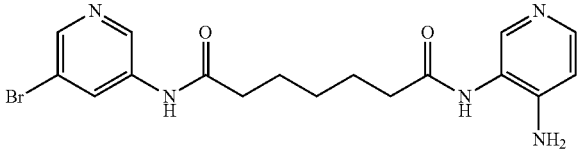 [SMILES: Nc1ccncc1NC(=O)CCCCCC(=O)Nc1cncc(Br)c1] |
| 15. | 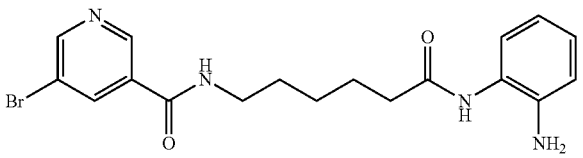 [SMILES: Nc1ccccc1NC(=O)CCCCCNC(=O)c1cncc(Br)c1] |
| 16. | 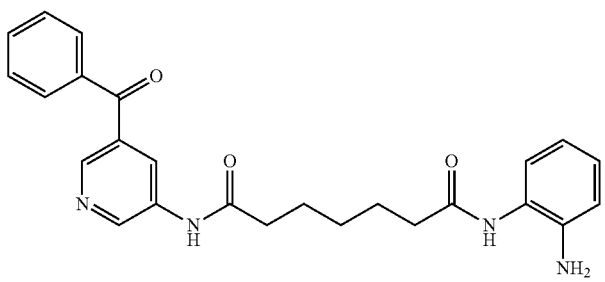 [SMILES: Nc1ccccc1NC(=O)CCCCCC(=O)Nc1cncc(C(=O)c2ccccc2)c1] |
| 17. | 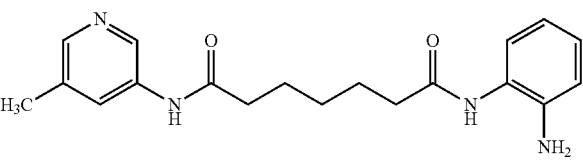 [SMILES: Cc1cncc(NC(=O)CCCCCC(=O)Nc2ccccc2N)c1] |
| 18. | 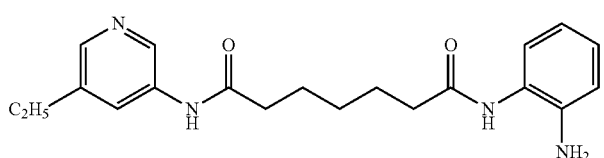 |
| 19. | 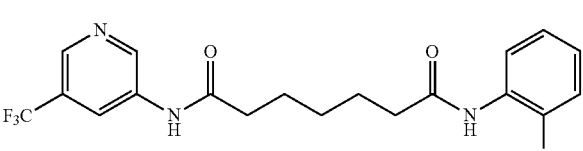 |
| 20. | 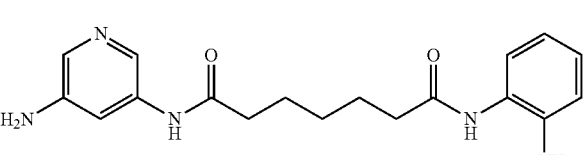 |

As used herein, the term "alkyl" refers to a straight or branched chain hydrocarbon having 1, 2, 3, 4, 5, 6, 7, 8, 9, 10, 11, 12, 13, 14, 15, 16, 17, 18, 19 or 20 carbon atoms. Optionally, an alkyl group may contain one or more unsaturated bonds (e.g. —C≡C—, and carbon-carbon triple bond).

As used herein, the term "cycloalkyl" refers to a non-aromatic cyclic hydrocarbon ring having from three to seven carbon atoms and which optionally includes an alkyl linker through which it may be attached, preferably a $C_1$-$C_6$ alkyl linker as defined above. Such a ring may be optionally fused to one or more cycloalkyl ring(s), aryl ring(s), and/or heteroaryl ring(s). Exemplary "cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a 3, 4, 5, 6, 7, 8, 9, 10, 11 or 12-membered cycloalkyl ring containing one or more heteroatomic substitutions on the ring selected from S, O or N. Such a ring may be optionally fused to one or more cycloalkyl ring(s), heterocyclic ring(s), aryl ring(s), and/or heteroaryl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, piperazine, and the like.

As used herein, the term "aryl" refers to an aromatic cyclic hydrocarbon ring (such as phenyl ring) and which optionally includes an alkyl linker through which it may be attached, preferably a $C_1$-$C_6$ alkyl linker as defined above. Such a ring may be optionally fused to one or more other aryl ring(s). Examples of "aryl" groups include, but are not limited to, phenyl, 2-naphthyl, 1-naphthyl, biphenyl, imidazolyl as well as substituted derivatives thereof.

As used herein, the term "heteroaryl" refers to an aromatic cyclic hydrocarbon ring containing one or more heteroatomic substitutions on the ring selected from S, O or N, and which optionally includes an alkyl linker through which it may be attached, preferably a $C_1$-$C_6$ alkyl linker as defined above. Such a ring may be optionally fused to one or more other aryl ring(s) and/or heteroaryl ring(s). Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzopyrrolyl, benzothiophenyl, indolyl, indazolyl, and substituted derivatives thereof.

As used herein, the term "halogen" or "halo" refers to fluorine (F), chlorine (Cl), bromine (Br) or iodine (I).

As used herein, the term "alkoxy" refers to an alkyl group wherein one or more hydrogen and/or carbon atoms are substituted with oxygen or hydroxyl group.

As used herein, the term "aryloxy" refers to an aryl group wherein one or more hydrogen atoms are substituted with oxygen or hydroxyl group.

As used herein, the term "alkylamino" refers to an alkyl group wherein one or more hydrogen and/or carbon atoms are substituted with nitrogen or amino group.

As used herein, the term "arylamino" refers to an amino group substituted with at least an aryl or heteroaryl group on nitrogen. In certain embodiments, the nitrogen is further substituted with one or more substituents selected from the group consisting of alkyl, cycloalkyl, heterocyclic, aryl and heteroaryl.

As used herein, the term "haloalkyl" refers to an alkyl group wherein one or more hydrogen and/or carbon atoms are substituted with halogen atom.

As used herein, the term "alkylcarbonyl" refers to R'—C(=O)—, wherein R' is an optionally substituted alkyl group.

As used herein, the term "arylcarbonyl" refers to R—C(=O)—, wherein R is an optionally substituted aryl group.

As used herein, the term "substituted" refers to substitution(s) on one or more atoms, wherein each atom may be substituted with one or more substituents described above. Further examples of substitutions include, without limitation, halogen, alkyl, alkoxy, alkylamino, haloalkyl, —CN, and alkylcarbonyl.

Unless otherwise specified, all substituents intend to include optionally substituted substituents, i.e. further substituted or not. For example, an alkyl group may be an unsubstituted alkyl group, or a substituted alkyl group as defined supra.

As used herein, a compound or a composition that is "pharmaceutically acceptable" is suitable for use in contact with the tissue or organ of a biological subject without excessive toxicity, irritation, allergic response, immunogenicity, or other problems or complications, commensurate with a reasonable benefit/risk ratio. If said compound or composition is to be used with other ingredients, said compound or composition is also compatible with said other ingredients.

As used herein, the term "solvate" refers to a complex of variable stoichiometry formed by a solute (e.g., compounds provided herein) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compound according to the invention.

As used herein, pharmaceutically acceptable salts of a compound refers to any pharmaceutically acceptable acid and/or base additive salt of the compound (e.g., compounds provided herein). Suitable acids include organic and inorganic acids. Suitable bases include organic and inorganic bases. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

According to some embodiments provided herein, a kit is provided that comprises one or more compounds disclosed herein or compositions or formulations thereof. In one embodiment, the kit may be used a research tool to investigate the effect of modulation of MEF2 by one or more transcription factor modulators on the cellular processes of which MEF2 is involved. In some embodiments, the cellular processes may include, but are not limited to, the transmission of extracellular signals to the genome and/or the activation of certain genetic programs in a cell. In some embodiments, the genetic programs may include, but are not limited to, genetic programs that control cell differentiation, proliferation, morphogenesis, survival and/or apoptosis.

II. Compositions

Provided herein in certain embodiments are compositions comprising one or more of the compounds provided herein. The compounds provided herein may contain one or more chiral atoms, or may otherwise be capable of existing as two or more stereoisomers, which are usually enantiomers and/or diastereomers. Accordingly, the compositions provided herein include mixtures of stereoisomers or mixtures of enantiomers, as well as purified stereoisomers, purified enantiomers, stereoisomerically enriched mixtures, or enantiomerically enriched mixtures. The compositions provided herein also include the individual isomers of the compound represented by the structures described above as well as any wholly or partially equilibrated mixtures thereof. The compositions provided herein also include the individual isomers of the compounds represented by the structures described above as mixtures with isomers thereof in which one or more chiral centers are inverted. Also, it is understood that all tautomers and mixtures of tautomers of the structures described above are included within the scope of the structures and preferably the structures corresponding thereto.

Racemates can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent. The diastereomer resolution can also be carried out by standard purification processes, such as, for example, chromatography or fractional crystallization.

It is also possible to obtain optically active compounds comprising the structure of the compounds disclosed herein by the methods described above by using starting materials which are already optically active.

III. Pharmaceutical Formulations

As used herein, a pharmaceutical formulation comprises a therapeutically effective amount of one or more of the compounds or compositions provided herein. In certain embodiments, the pharmaceutical formulation further comprises a pharmaceutically acceptable carrier.

As used herein, a "therapeutically effective amount," "therapeutically effective concentration" or "therapeutically effective dose" is an amount which, as compared to a corresponding subject who has not received such amount, results in improved treatment, healing, prevention, or amelioration of a disease, disorder, or side effect, or a decrease in the rate of advancement of a disease or disorder.

This amount will vary depending upon a variety of factors, including but not limited to the characteristics of the compounds, compositions, or pharmaceutical formulations thereof (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier or carriers in the formulation, and the route of administration. One skilled in the clinical and pharmacological arts will be able to determine an effective amount or therapeutically effective amount through routine experimentation, namely by monitoring a cell's or subject's response to administration of the one or more compounds disclosed herein or the pharmaceutical formulation thereof and adjusting the dosage accordingly. A typical dosage may range from about 0.1 mg/kg to about 100 mg/kg or more, depending on the factors mentioned above. In other embodiments, the dosage may range from about 0.1 mg/kg to about 100 mg/kg; or about 1 mg/kg to about 100 mg/kg; or about 5 mg/kg up to about 100 mg/kg. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

As used herein, the term "about" refers to ±10%, ±5%, or ±1%, of the value following "about."

A "pharmaceutically acceptable carrier" is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body. Each carrier is "pharmaceutically acceptable" in the sense of being compatible with the other ingredients, e.g., the compounds or compositions described herein or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Pharmaceutically acceptable carriers are well known in the art and include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations.

The pharmaceutical formulations disclosed herein may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the one or more compounds or compositions thereof in the pharmaceutical formulations provided herein can vary widely, and will be selected primarily based on fluid volumes, viscosities, body weight and the like in accordance with the particular mode of administration selected and the biological subject's needs. For example, the concentration of the one or more compounds disclosed herein can be about 0.0001% to about 100%, about 0.001% to about 50%, about 0.01% to about 30%, about 0.1% to about 20%, about 1% to about 10% wt.

A suitable pharmaceutically acceptable carrier may be selected taking into account the chosen mode of administration, and the physical and chemical properties of the compounds.

One skilled in the art will recognize that a pharmaceutical formulation containing the one or more compounds provided herein or compositions thereof can be administered to a subject by various routes including, without limitation, orally or parenterally, such as intravenously. The composition may also be administered through subcutaneous injection, subcutaneous embedding, intragastric, topical, and/or vaginal administration. The composition may also be administered by injection or intubation.

In one embodiment, the pharmaceutical carrier may be a liquid and the pharmaceutical formulation would be in the form of a solution. In another embodiment, the pharmaceutically acceptable carrier is a solid and the pharmaceutical formulation is in the form of a powder, tablet, pill, or capsules. In another embodiment, the pharmaceutical carrier is a gel and the pharmaceutical formulation is in the form of a suppository or cream.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to about 99% of the one or more compounds disclosed herein. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the one or more compounds provided herein or compositions thereof, the pharmaceutical formulations may also include suitable diluents, preservatives, solubilizers, emulsifiers, adjuvant and/or carriers.

The pharmaceutical formulation can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Additional pharmaceutical formulations will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT/US93/0082948 which is incorporated herein by reference as if fully set forth herein for the techniques of controlled release of porous polymeric microparticles for the delivery of pharmaceutical formulations. Additional examples of sustained-release preparations include semipermeable polymer matrices in the form of shaped articles, e.g. films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate or poly-D (−)-3-hydroxybutyric acid. Sustained-release compositions also include liposomes, which can be prepared by any of several methods known in the art.

IV. Methods of Preparation

Another aspect of the invention relates to the preparation of the compounds disclosed herein.

In one embodiment, one or more compounds disclosed herein are synthesized according to Scheme 1, wherein A ring, B ring, and $L_1$ are defined as the same as above, and $R_0$ represents one or more substituents on B ring as defined the same as above (e.g. $R_1$~$R_5$):

Scheme 1.

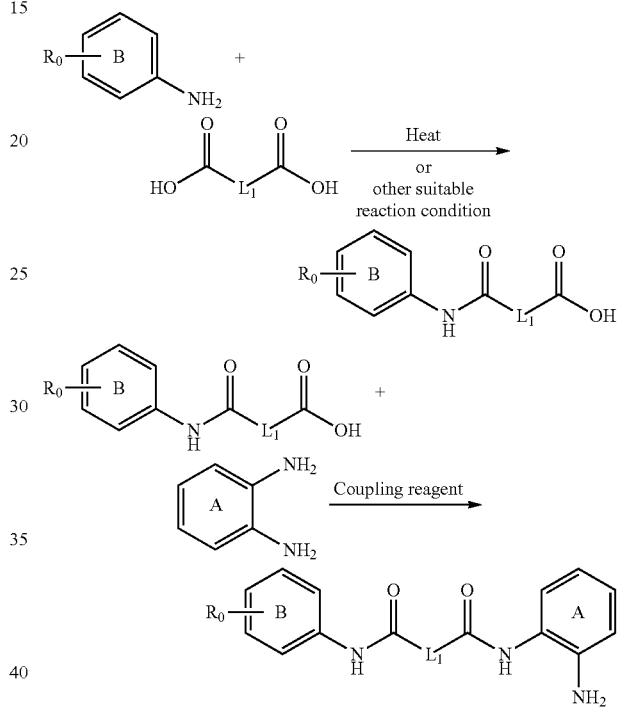

In certain embodiments, $L_1$ is —$(CH_2)_n$—, where n is 4, 5, 6, 7, or 8.

In one embodiment, one or more compounds disclosed herein are synthesized according to Scheme 2, wherein A ring, B ring, and $L_1$ are defined the same as above, and $R_0$ represents one or more substituents on B ring as defined the same as above (e.g. $R_1$~$R_5$):

Scheme 2.

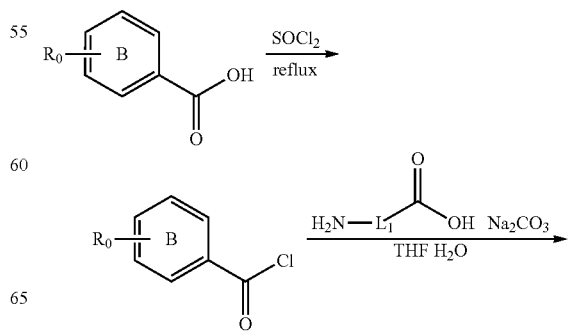

-continued

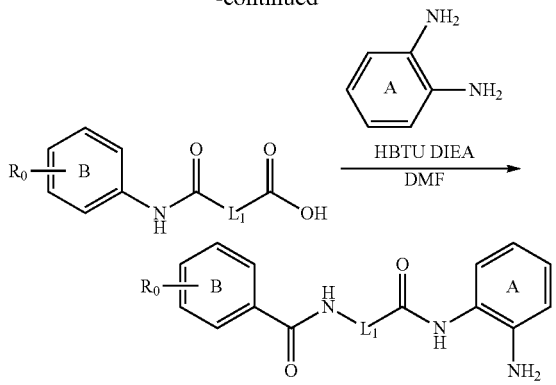

In certain embodiments, $L_1$ is $—(CH_2)_n—$, where n is 4, 5, 6, 7, or 8.

More specific examples of synthesis are described in the examples. A person of ordinary skill in the art would recognize the synthesis of the compounds disclosed herein using conventional organic synthesis methods.

V. Methods of Treatment

Another aspect described herein relates to a method of treating a condition regulatable by a transcription factor and/or cofactor comprising administering to the subject a therapeutically effective amount of one or more of the compounds, compositions, or pharmaceutical formulations disclosed herein.

Optimal dosages to be administered may be determined by those skilled in the art, and will vary with the particular compounds, compositions, or formulations used, the strength of the preparation, the mode of administration, and the advancement of the disease condition. Additional factors depending on the particular subject being treated, include, without limitation, subject age, weight, gender, diet, time of administration, time and frequency of administration, drug combination(s), reaction sensitivities, and response to therapy. Administration may be effected continuously or intermittently. In any treatment regimen, the compound, composition, or pharmaceutical formulation may be administered to a subject either singly or in a cocktail containing two or more compounds or compositions thereof, other therapeutic agents, or the like, including, but not limited to, tolerance-inducing agents, potentiators and side-effect relieving agents. All of these agents are administered in generally-accepted efficacious dose ranges such as those disclosed in the Physician's Desk Reference, 41st Ed., Publisher Edward R. Barnhart, N.J. (1987), which is herein incorporated by reference as if fully set forth herein. In certain embodiments, an appropriate dosage level will generally be about 0.001 to about 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day. In some embodiments, the daily dosage may be between about $10^{-6}$ g/kg to about 5 g/kg of body weight.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

In some embodiments, the one or more compounds provided herein or compositions or pharmaceutical formulations thereof may be administered in a combination manner in a treatment method. "In a combination manner" as used herein, means in the course of treating the same subject using two or more agents (e.g. transcription factor modulators disclosed herein), in any order. This includes simultaneous administration (in the same or separate formulations), as well as administration in a temporally spaced order of up to several days apart. Such combination treatment may also include more than a single administration of any one or more of the agents. Further, the administration of the two or more agents may be by the same or different routes of administration.

In some embodiments, the condition is a disease related to dysfunction of a transcription factor and/or cofactor. In certain of these embodiments, the compounds provided herein are transcription factor modulators. In certain embodiments, the transcription factor is selected from the group consisting of forkhead box protein P3 (FOXP3) and myocyte enhancer factor 2 (MEF2). In certain embodiments, the transcription factor modulators binds to a highly conserved hydrophobic groove on the MADS-box of MEF2.

In certain embodiments where the compounds provided herein are transcription factor modulators, the compounds may selectively bind a transcription factor or cofactor.

In certain embodiments where the compounds provided herein are transcription factor modulators, the compounds may modulate the function of transcription factors that are associated with certain diseases.

In some embodiments where the compounds provided herein are transcription factor modulators, the compounds may modulate the interaction between a transcription factor and a transcription cofactor. In some embodiments, the transcription cofactors are transcription co-activators and/or co-repressors. In certain embodiments, the compounds may directly bind the transcription factor and/or cofactor. In certain embodiments, the transcription cofactor is selected from the group consisting of calcineurin binding protein 1, histone deacetylases (HDACs), E1A binding protein P300, CREB binding protein, extracellular signal-regulated kinase 5, myoblast differentiation protein, Smad protein, nuclear factor of activated T cell, myocardin, and positive transcription elongation factor b. In some embodiments, the transcription cofactor is a class IIa HDAC.

In some embodiments where the compounds provided herein are transcription factor modulators, the compounds may modulate the interaction between a transcription factor and a transcription cofactor, wherein the transcription cofactor is not an HDAC. In one embodiment, the transcription cofactor is not a class IIa HDAC. In other embodiments, the one or more compounds may include, but are not limited to, CC6.

Another aspect of the present disclosure relates to the use of one or more compounds provided herein or compositions or pharmaceutical formulations thereof in the manufacture of a medicament. In certain embodiments, the medicament is for the treatment of a condition regulatable by a transcription factor and/or cofactor. For these aspects, the compounds, compositions, and pharmaceutical formulations, the transcription factors and/or cofactors, and the conditions regulatable by the transcription factor and/or cofactor are the same as disclosed above, and the treatment of the condition is the same as described herein.

The following examples are intended to illustrate various embodiments of the present disclosure. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entireties, as if fully set forth herein.

EXAMPLES

Example 1

Synthesis of CC No. 1 (N$^1$-(2-aminophenyl)-N$^7$-(pyridin-3-ylmethyl)heptanediamide)

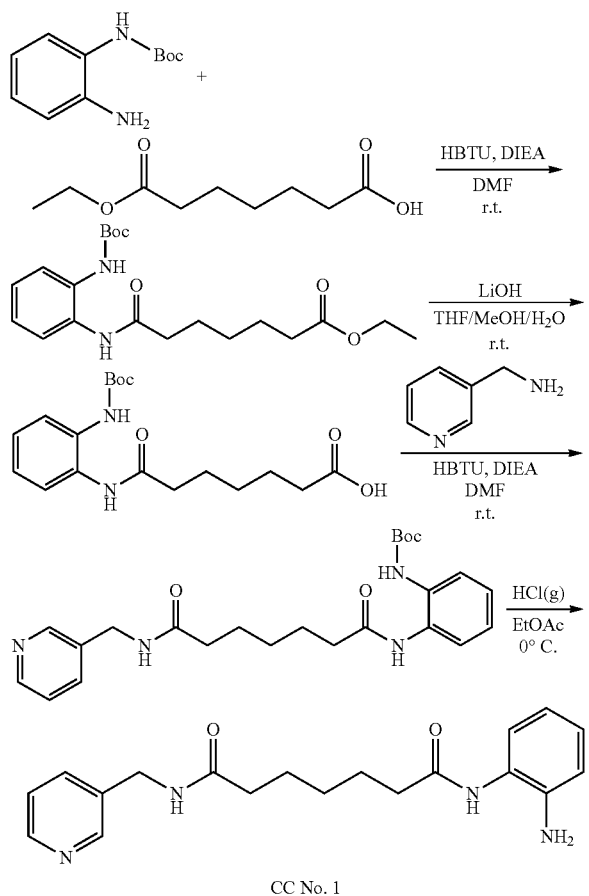

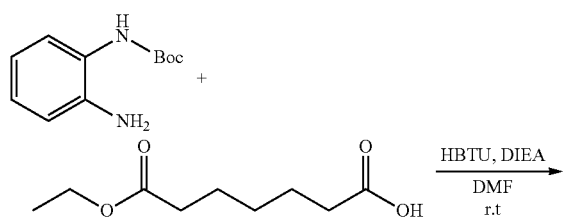

CC No. 1

As used herein, "r.t." "r.t" "rt." or "rt" is room temperature.

1) Synthesis of ethyl 7-((2-((tert-butoxycarbonyl)amino)phenyl)amino)-7-oxoheptanoate

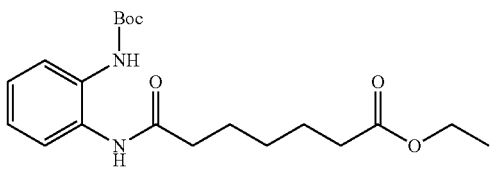

To a solution of 7-ethoxy-7-oxoheptanoic acid (2.0 g, 10.6 mmol) in DMF (50 mL) were added HBTU (4.4 g, 11.6 mmol), DIEA (4.1 g, 31.8 mmol) at room temperature. The resulting mixture was stirred for 10 min, then tert-butyl (2-aminophenyl)carbamate (2.43 g, 11.7 mmol) was added to the reaction solution. The reaction mixture was stirred for 12 h at room temperature. The reaction was quenched with water (200 mL). The resulting mixture was extracted by EtOAc (200 mL×2). The organic layers were combined, dried with anhydrous Na$_2$SO$_4$ and concentrated under reduced pressure. The resulting solid was purified by column chromatography (elute: EtOAc:PE (petroleum ether)=1:4) to afford the desired compound (3.7 g, yield 92.1%) as a light yellow oil.

2) Synthesis of 7-((2-((tert-butoxycarbonyl)amino)phenyl)amino)-7-oxoheptanoic acid

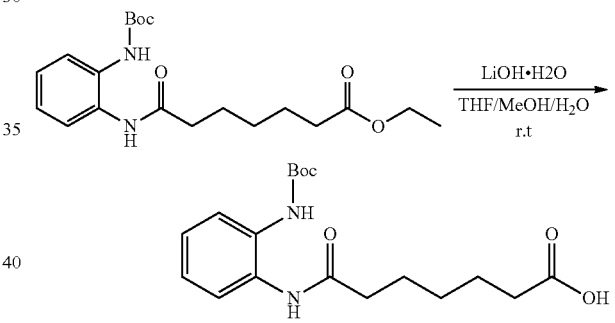

To a solution of ethyl 7-((2-((tert-butoxycarbonyl)amino)phenyl)amino)-7-oxoheptanoate (3.7 g, 9.7 mmol) in THF/MeOH/H$_2$O (V:V:V=4:1:1) (50 mL) were added lithium hydroxide monohydrate (1.3 g, 29.1 mmol). The mixture was stirred at room temperature for 3 hours and quenched with water (200 mL). To the solution was added 1M HCl to adjust the pH value to 2-3, then a white solid precipitated and was filtered to afford the desired compound (3.3 g, yield 96.5%).

3) Synthesis of tert-butyl (2-(7-oxo-7-((pyridin-3-ylmethyl)amino)heptanamido)phenyl)carbamate

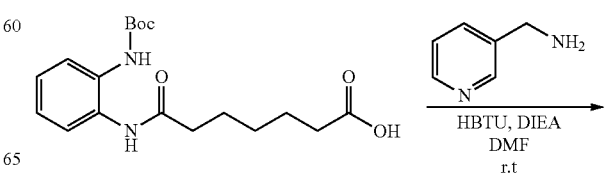

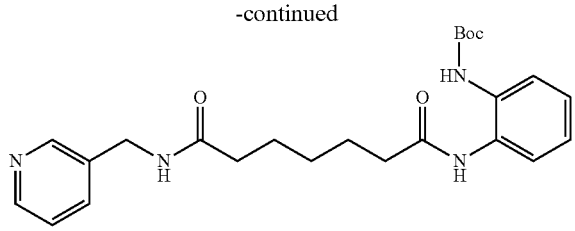

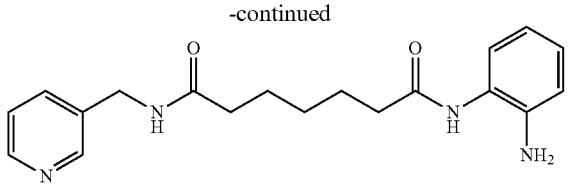

To a solution of 7-((2-((tert-butoxycarbonyl)amino)phenyl)amino)-7-oxoheptanoic acid (1.2 g, 3.42 mmol) in DMF (10 mL) were added HBTU (1.43 g, 3.76 mmol), DIEA (1.3 g, 10.3 mmol) at room temperature. The resulting mixture was stirred for 10 min, then tpyridin-3-ylmethanamine (1.43 g, 3.76 mmol) was added to the reaction solution. The reaction mixture was stirred for 12 h at room temperature. The reaction was quenched with water (100 mL). The resulting mixture was extracted by EtOAc (100 mL×2). The organic layers were combined, dried with anhydrous Na$_2$SO$_4$ and concentrated under reduced pressure. The resulting solid was purified by column chromatography (elute: EtOAc:MeOH=100:1) to afford desired compound (1.2 g, yield 79.7%) as an off-white solid.

Into a solution of tert-butyl (2-(7-oxo-7-((pyridin-3-ylmethyl)amino)heptanamido)phenyl)carbamate (1.2 g, 2.73 mmol) in EtOAc (50 mL) were passed HCl (gas) at 0° C. The mixture was stirred for 30 min at 0° C. under HCl (gas). A white solid precipitated and was filtered. The white solid was collected and poured into a solution of 5% Na$_2$CO$_3$ in water (100 mL). The resulting mixture was extracted by EtOAc (100 mL×2). The organic layers were combined, dried with anhydrous Na$_2$SO$_4$ and concentrated under reduce pressure. The crude solid was recrystallized in EtOAc to afford the desired compound (0.6 g, yield 64.6%) as an off-white solid.

Mp: 134.4-134.5° C., $^1$H NMR (400 MHz, DMSO): δ 1.28-1.30 (m, 2H), 1.53-1.58 (m, 4H), 2.13-2.15 (m, 2H), 2.27-2.30 (m, 2H), 4.27-4.29 (d, 2H), 4.81 (s, 2H), 6.50-6.56 (m, 1H), 6.69-6.72 (m, 1H), 6.86-6.88 (m, 1H), 7.13-7.16 (m, 1H), 7.31-7.35 (m, 1H), 7.61-7.64 (m, 1H), 8.35-8.46 (m, 3H), 9.29 (s, 1H), LCMS found 341.2 [M+H]$^+$, HPLC (254 nm, purity 99%).

4) Synthesis of N$^1$-(2-aminophenyl)-N$^7$-(pyridin-3-ylmethyl)heptanediamide

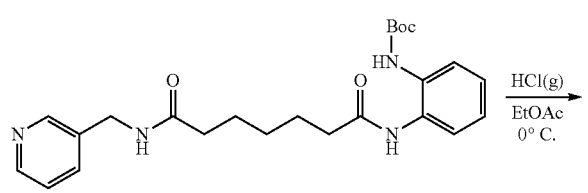

Example 2

Synthesis of CC No. 2, N$^1$-(2-aminophenyl)-N$^7$-(3-hydroxyphenyl)heptanediamide

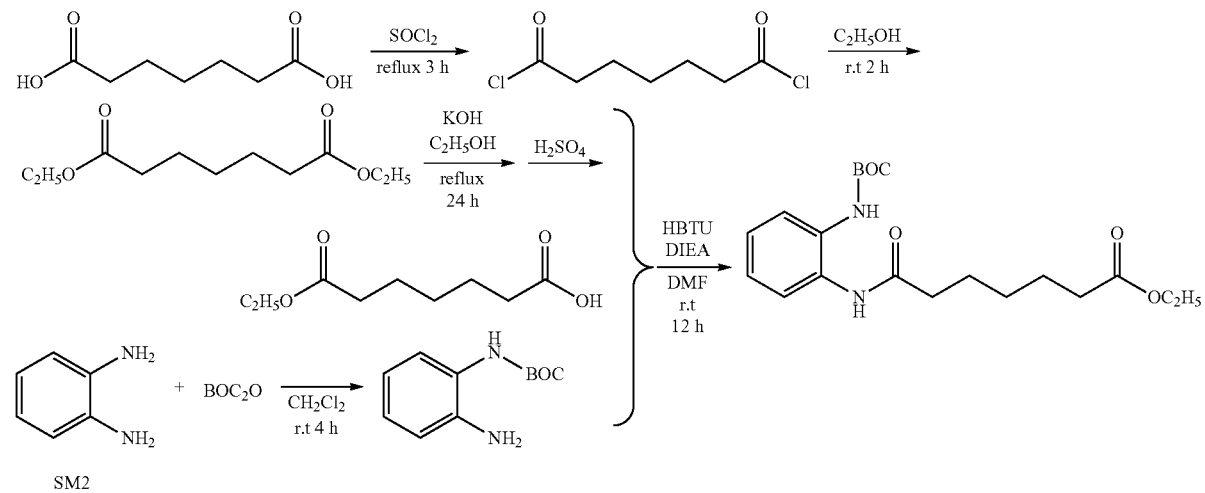

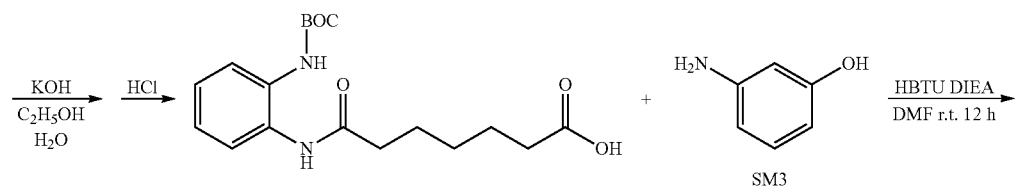

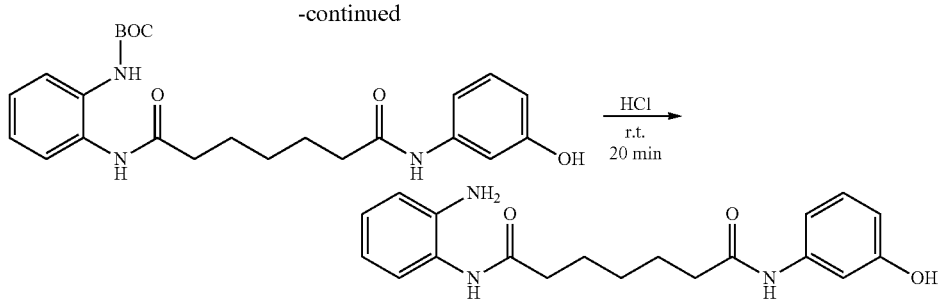

CC No. 2

1) Synthesis of heptanedioyl dichloride

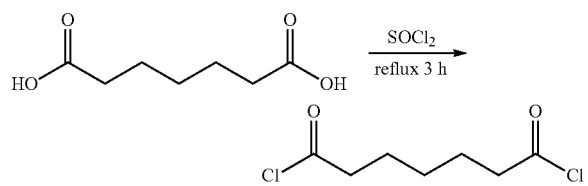

A mixture of heptanedioic acid (50 g, 0.31 mol) in SOCl₂ (120 mL) was stirred at 75° C. for 3 hours and then concentrated under reduced pressure. The resulting colorless liquid was used directly for next step without further purification (60 g, yield 98%).

2) Synthesis of diethyl heptanedioate

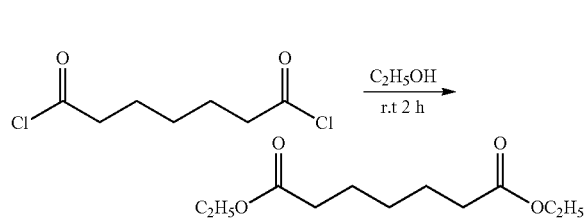

To a solution of ethanol (200 mL) was added dropwise heptanedioyl dichloride (60 g, 0.30 mol) at 0° C. over 0.5 hour, then the reaction was stirred at room temperature for 2 hours and then concentrated under reduced pressure. The resulting mixture was poured into water and extracted with EtOAc (250 mL). The organic layers were washed with saturated aqueous solution of Na₂CO₃, dried over Na₂SO₄ and concentrated to give the desired compound (65 g, yield 99%).

3) Synthesis of 7-ethoxy-7-oxoheptanoic acid

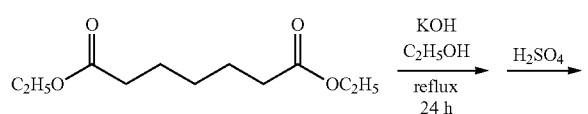

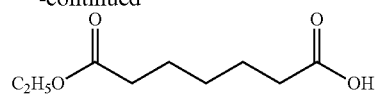

To a solution of diethyl heptanedioate (65 g, 0.30 mol) in ethanol (400 mL) was added KOH (16.8 g, 0.30 mmol). The mixture was stirred at 80° C. for 24 hours and concentrated under reduced pressure. The resulting mixture was poured into water and the pH value of the solution was adjusted to 1 by concentrated H₂SO₄. After removal of the solvent, the crude product was purified by flash chromatography SiO₂ (EtOH:EtOAc=1:10) to give the desired compound (38 g, yield 67%).

(4) Synthesis of tert-Butyl (2-aminophenyl)carbamate

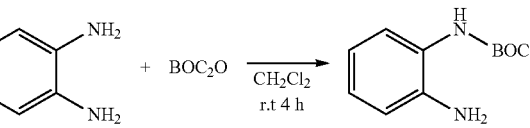

To a solution of benzene-1,2-diamine (20 g, 0.185 mol), triethylamine (22.4 g, 0.222 mol) in CH₂Cl₂ (400 mL) was added Boc anhydride (42.4 g, 0.194 mmol). The mixture was stirred at room temperature for 4 hours. The reaction was washed with water (200 mL×3) and brine (200 mL×3), dried over Na₂SO₄ and concentrated under reduced pressure to give the desired compound which was purified by flash chromatography SiO₂ (EtOAc:PE=1:10) (27 g, yield 70%).

(5) Synthesis of Ethyl 7-((2-((tert-butoxycarbonyl)amino)phenyl)amino)-7-oxoheptanoate

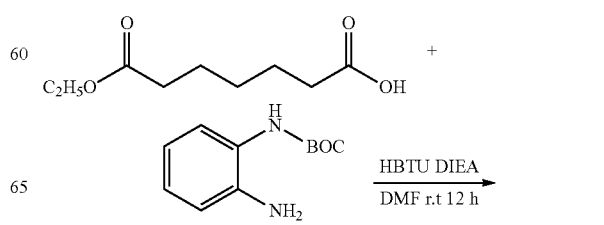

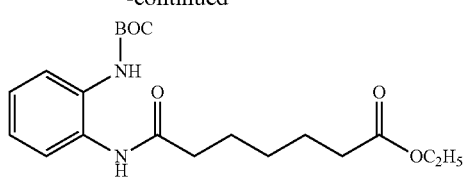
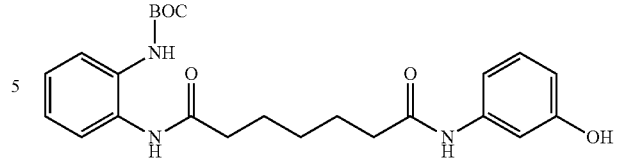

To a solution of 7-ethoxy-7-oxoheptanoic acid (7.23 g, 385 mmol) in DMF (150 mL) was added tert-Butyl(2-aminophenyl)carbamate (8 g, 385 mmol), HBTU (14.6 g, 385 mmol), DIEA (20 mL, 1155 mmol). The mixture was stirred at room temperature for 12 hours. The resulting mixture was poured into water and extracted by EtOAc (200 mL×3). The organic layers were combined and washed with saturated aqueous solution of $Na_2CO_3$, dried over $Na_2SO_4$ and then concentrated to give the desired compound (14 g, yield 96.3%).

(6) Synthesis of 7-((2-((tert-butoxycarbonyl)amino)phenyl)amino)-7-oxoheptanoic acid To a solution of 7-((2-((tert-butoxycarbonyl)amino)phenyl)amino)-7-oxoheptanoic acid (1.0 g, 2.85 mmol) in DMF (20 mL) was added 3-aminophenol (0.31 g, 2.85 mmol), HBTU (1.1 g, 2.85 mmol), DIEA (2 mL, 11.4 mmol). The mixture was stirred at room temperature for 12 hours. The resulting mixture was poured into water and extracted by EtOAc (100 mL×3). The organic layers were combined and washed with saturated aqueous solution of $Na_2CO_3$, dried over $Na_2SO_4$ and then the resulting solution was used directly for next step without further purification.

(8) Synthesis of $N^1$-(2-aminophenyl)-$N^7$-(3-hydroxyphenyl)heptanediamide

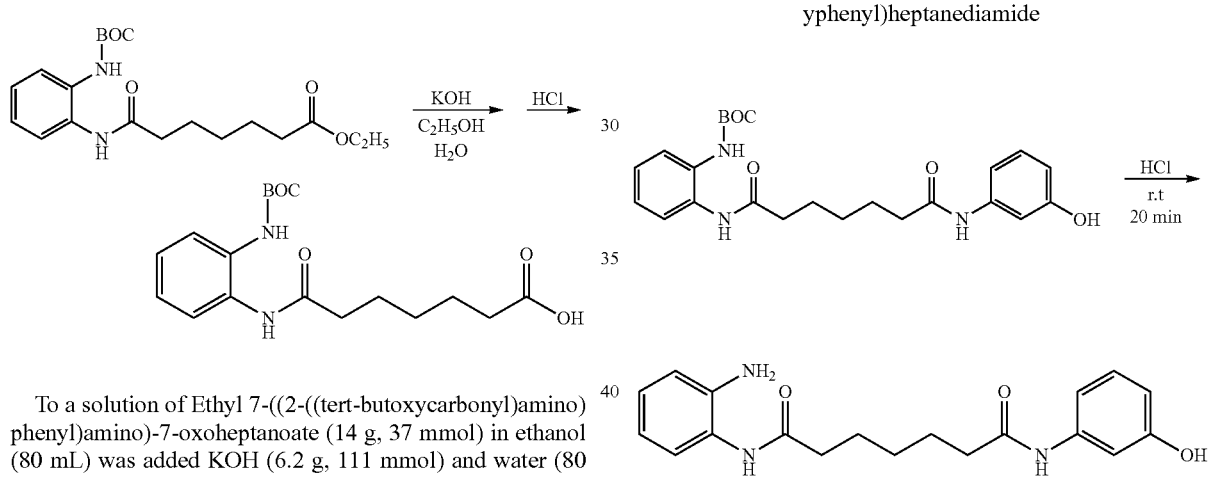

To a solution of Ethyl 7-((2-((tert-butoxycarbonyl)amino)phenyl)amino)-7-oxoheptanoate (14 g, 37 mmol) in ethanol (80 mL) was added KOH (6.2 g, 111 mmol) and water (80 mL). The mixture was stirred at room temperature for 4 hours and concentrated under reduced pressure. The pH value of the solution was adjusted to 4 by concentrated HCl. The resulting mixture was extracted by EtOAc (200 mL×3). The organic layers were combined and dried over $Na_2SO_4$, then concentrated to give the desired compound (12 g, yield 92.5%).

(7) Synthesis of tert-Butyl (2-(7-((3-hydroxyphenyl)amino)-7-oxoheptanamido)phenyl)carbamate

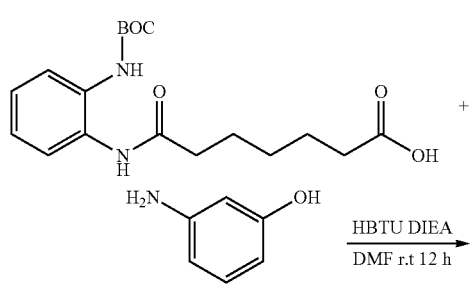

The solution of tert-Butyl (2-(7-((3-hydroxyphenyl)amino)-7-oxoheptanamido)phenyl)carbamate in EtOAc was stirred at 0° C. and bubbled with HCl gas for 20 min. The pH value of the solution was adjusted to 6 by saturated aqueous solution of $Na_2CO_3$. The aqueous phase was extracted with EtOAc (100 mL). The organic layers were combined and dried over $Na_2SO_4$ and then concentrated to give the crude product. The crude product was purified by flash chromatography $SiO_2$ (EtOAc) to give desired compound CC No. 2 (0.25 g, yield 25.7%).

1 H NMR (400 MHz, DMSO): δ 1.30-1.35 (m, 2 H), 1.55-1.61 (m, 4H), 2.21-2.31 (t, 4 H), 4.80 (s, 2 H), 6.37-6.40 (m, 1 H), 6.47-6.52 (m, 1 H), 6.66-6.69 (m, 1 H), 6.83-6.92 (m, 2 H), 6.98-7.04 (m, 1 H), 7.10-7.16 (m, 2 H), 9.06 (s, 1 H), 9.29 (s, 1 H), 9.70 (s, 1 H). LCMS found 342 [M+H]+, HPLC (254 nm, purity 100%).

Example 3

Synthesis of CC No. 3, $N^1$-(2-aminophenyl)-$N^7$-(4-hydroxyphenyl)heptanediamide

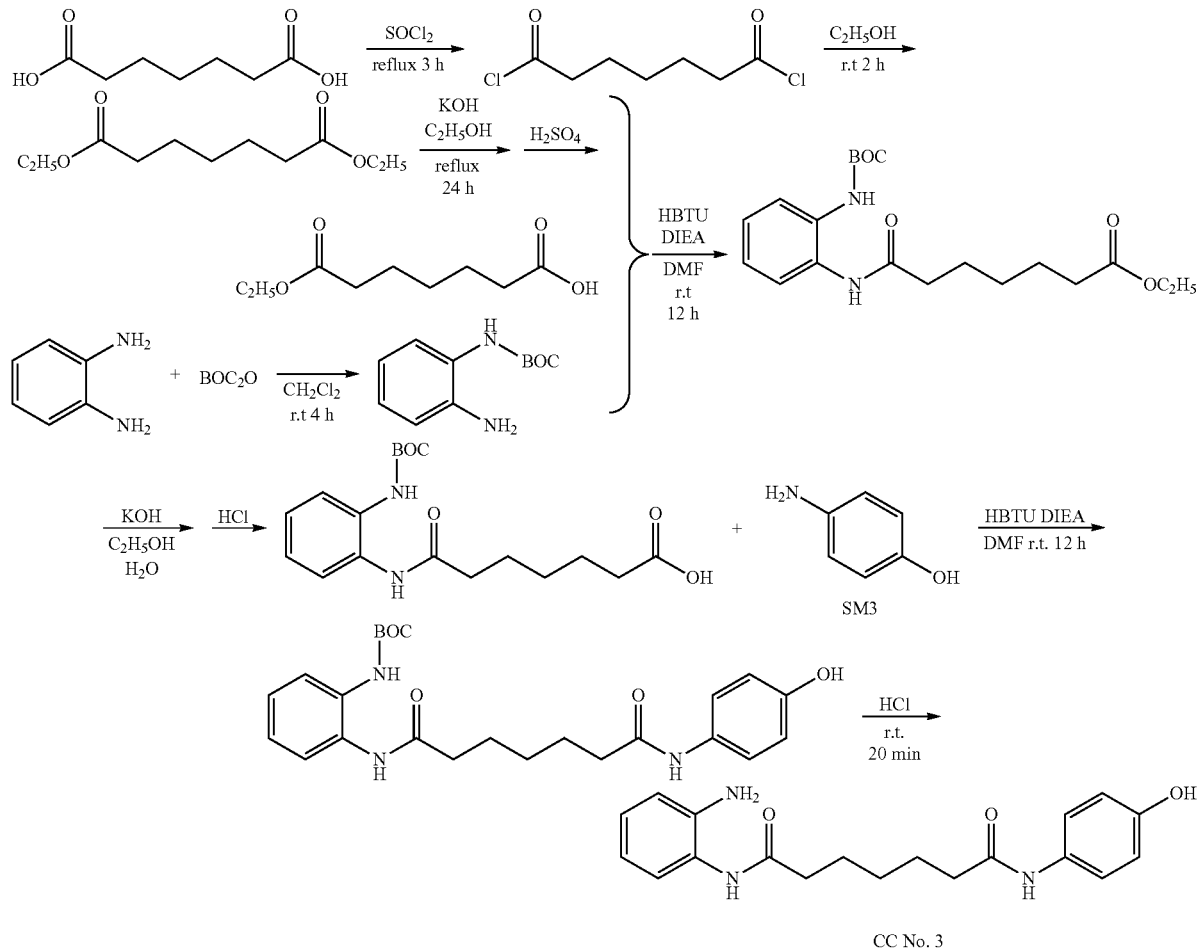

CC No. 3

(1) Synthesis of heptanedioyl dichloride

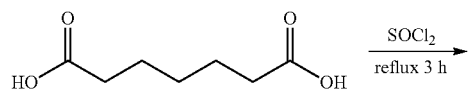

A mixture of heptanedioic acid (50 g, 0.31 moL) in SOCl$_2$ (120 mL) was stirred at 75° C. for 3 hours and then concentrated under reduced pressure. The resulting colorless liquid was used directly for next step without further purification (60 g, yield 98%).

(2) Synthesis of diethyl heptanedioate

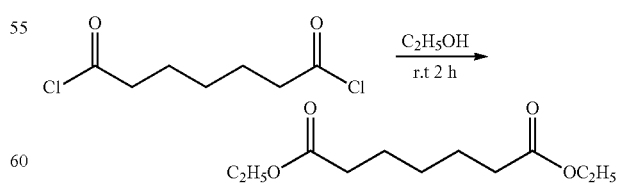

To a solution of Ethanol (200 mL) was added dropwise heptanedioyl dichloride (60 g, 0.30 moL) at 0° C. over 0.5 hour, then the reaction was stirred at room temperature for 2 hours and concentrated under reduced pressure. The resulting mixture was poured into water and extracted with EtOAc (250

(3) Synthesis of 7-ethoxy-7-oxoheptanoic acid

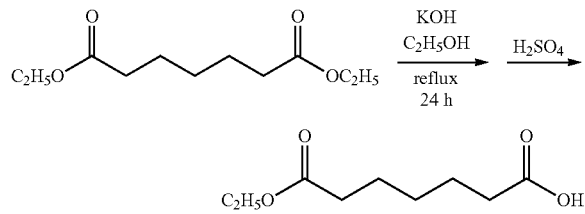

To a solution of diethyl heptanedioate (65 g, 0.30 mol) in Ethanol (400 mL) was added KOH (16.8 g, 0.30 mmol). The mixture was stirred at 80° C. for 24 hours, and concentrated under reduced pressure. The resulting mixture was poured into water and the pH value of the solution was adjusted to 1 by concentrated $H_2SO_4$. After removal of the solvent, the crude product was purified by flash chromatography $SiO_2$ (EtOH:EtOAc=1:10) to give the desired compound (38 g, yield 67%).

(4) Synthesis of tert-Butyl (2-aminophenyl)carbamate

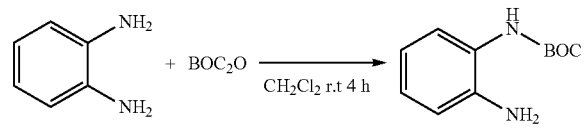

To a solution of benzene-1,2-diamine (20 g, 0.185 mol), triethylamine (22.4 g, 0.222 moL) in $CH_2Cl_2$ (400 mL) was added $Boc_2O$ (42.4 g, 0.194 mmol). The mixture was stirred at room temperature for 4 hours. The reaction was washed with water (200 mL×3) and brine (200 mL×3), dried over $Na_2SO_4$ and concentrated under reduced pressure to give the desired compound which was purified by flash chromatography $SiO_2$ (EtOAc:PE=1:10) (27 g, yield 70%).

(5) Synthesis of Ethyl 7-((2-((tert-butoxycarbonyl)amino)phenyl)amino)-7-oxoheptanoate

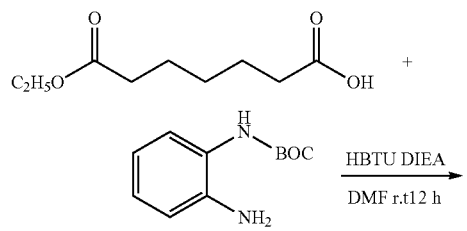

-continued

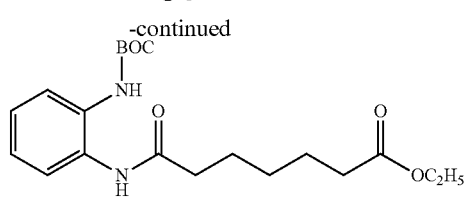

To a solution of 7-ethoxy-7-oxoheptanoic acid (7.23 g, 385 mmol) in DMF (150 mL) was added tert-butyl(2-aminophenyl)carbamate (8 g, 385 mmol), HBTU (14.6 g, 385 mmol), DIEA (20 mL, 1155 mmol). The mixture was stirred at room temperature for 12 hours. The resulting mixture was poured into water and extracted by EtOAc (200 mL×3). The organic layers were combined and washed with saturated aqueous solution of $Na_2CO_3$, dried over $Na_2SO_4$ and then concentrated to give the desired compound (14 g, yield 96.3%).

(6) Synthesis of 7-((2-((tert-butoxycarbonyl)amino)phenyl)amino)-7-oxoheptanoic acid

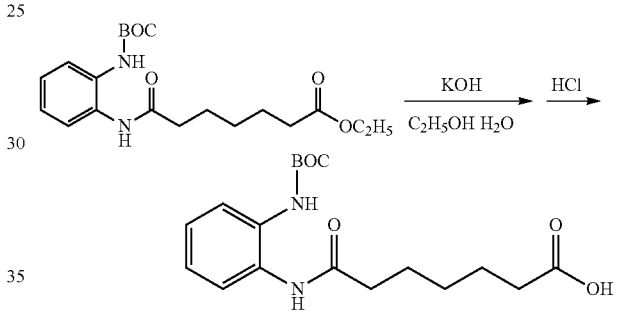

To a solution of Ethyl 7-((2-((tert-butoxycarbonyl)amino)phenyl)amino)-7-oxoheptanoate (14 g, 37 mmol) in Ethanol (80 mL) was added KOH (6.2 g, 111 mmol) and water (80 mL). The mixture was stirred at room temperature for 4 hours, and then concentrated under reduce pressure. The pH value of the solution was adjusted to 4 by concentrated HCl. The resulting mixture was extracted by EtOAc (200 mL×3). The organic layers were combined and dried over $Na_2SO_4$, then concentrated to give the desired compound (12 g, yield 92.5%).

(7) Synthesis of tert-Butyl (2-(7-((4-hydroxyphenyl)amino)-7-oxoheptanamido)phenyl)carbamate

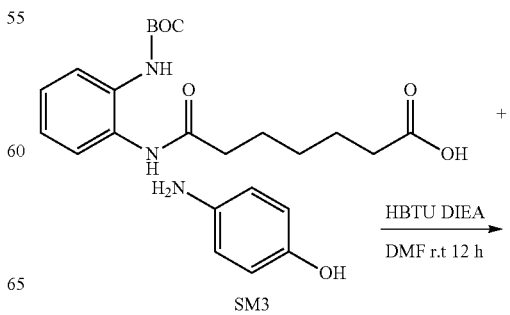

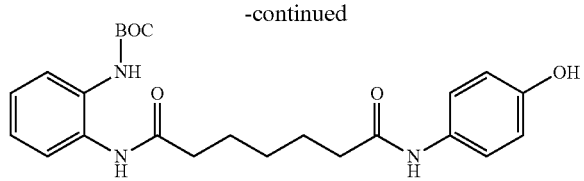

To a solution of 7-((2-((tert-butoxycarbonyl)amino)phenyl)amino)-7-oxoheptanoic acid (1.0 g, 2.85 mmol) in DMF (20 mL) was added 4-aminophenol (0.31 g, 2.85 mmol), HBTU (1.1 g, 2.85 mmol), DIEA (2 mL, 11.4 mmol). The mixture was stirred at room temperature for 12 hours. The resulting mixture was poured into water and extracted by EtOAc (100 mL×3). The organic layers were combined and washed with saturated aqueous solution of $Na_2CO_3$, dried over $Na_2SO_4$ and then the resulting residue was used directly for the next step without further purification.

(8) Synthesis of $N^1$-(2-aminophenyl)-$N^7$-(4-hydroxyphenyl)heptanediamide

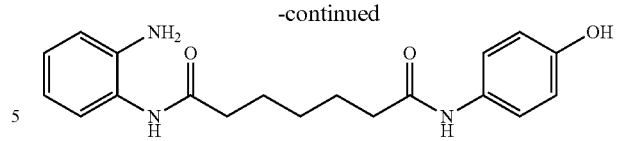

The solution of tert-Butyl (2-(7-((4-hydroxyphenyl)amino)-7-oxoheptanamido)phenyl)carbamate in EtOAc was stirred at 0° C. and bubbled with the gas of HCl for 20 min. The pH value of the solution was adjusted to 6 by saturated aqueous solution of $Na_2CO_3$. The aqueous phase was extracted with EtOAc (100 mL). The organic layers were combined and dried over $Na_2SO_4$ and then concentrated to give the crude product. The crude product was purified by flash chromatography $SiO_2$ (EtOAc) to give desired compound CC No. 3 (0.18 g, yield 18.5%).

1H NMR (400 MHz, DMSO): δ 1.28-1.34 (m, 2 H), 1.53-1.60 (m, 4 H), 2.20-2.31 (t, 4 H), 4.78 (s, 2 H), 6.47-6.52 (m, 1 H), 6.62-6.69 (m, 3 H), 6.83-6.85 (m, 1 H), 7.10-7.13 (m, 1 H), 7.31-7.34 (m, 2 H), 9.05 (s, 1 H), 9.09 (s, 1 H), 9.56 (s, 1 H). LCMS found 342 [M+H]+, HPLC (254 nm, purity 100%).

Example 4

Synthesis of CC No. 4, $N^1$-(4-aminopyridin-3-yl)-$N^7$-(3-bromophenyl)heptanediamide CC No.4

(1) Synthesis of tert-butyl 3-aminopyridin-4-ylcarbamate

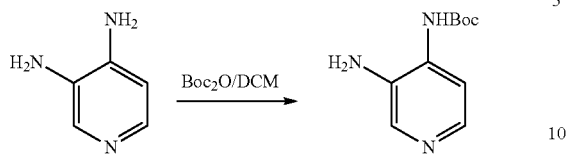

To a suspension of 3,4-diaminopyridine (4.18 g, 37.5 mmol) in DCM (40 mL) was added dropwise di-tertbutyldicarbonate (8.4 g, 37.5 mmol) in DCM (10 mL). The reaction was allowed to stir at room temperature overnight. 1N HCl (43 mL) was added dropwise and the organic layer was separated. The aqueous layer was extracted with DCM (75 mL) and the organic extracts were discarded. To the aqueous layer was added DCM (75 mL). The mixture was stirred and $K_2CO_3$ (4.1 g) was added. The resulting pH of the aqueous layer was 8-9. The layers were separated and the aqueous layer was extracted with DCM (75 mL×2). The organic extracts were combined, dried over $Na_2SO_4$, filtered and concentrated in a vacuum. The product was crystallized from MTBE and hexanes at 0° C. to provide desired compound (6.0 g, yield 75%).

(2) Synthesis of tert-butyl 3-(N-1-(3-bromophenyl) heptanediamido)pyridin-4-ylcarbamate

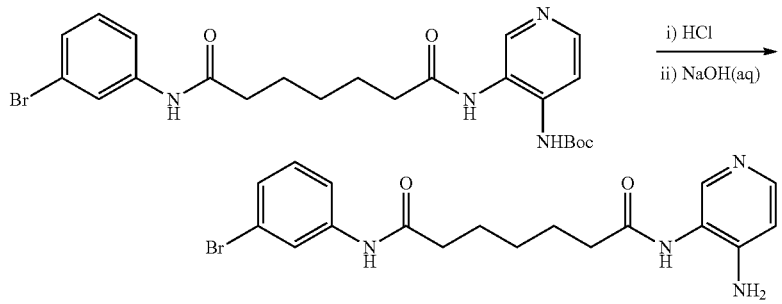

To a solution of 6-(3-bromophenylcarbamoyl)hexanoic acid (0.3 g, 0.95 mmol) in DMF (30 mL) were added HBTU (0.37 g, 0.98 mmol), DIEA (0.14 g, 1.09 mmol) at rt. The resulting mixture was stirred at 80° C. for 72 hours, cooled to room temperature and quenched by water. The resulting mixture was extracted with EtOAc (30 mL×3). The EtOAc layers were combined and dried, concentrated under reduce pressure to give a residue, which was purified by flash chromatography on $SiO_2$ (Hex:EtOAc=2:1) to give desired compound (0.1 g, yield 21%).

(3) Synthesis of $N^1$-(4-aminopyridin-3-yl)-$N^7$-(3-bromophenyl)heptanediamide)

To a solution of tert-butyl 3-(N1-(3-bromophenyl)heptanediamido)pyridin-4-ylcarbamate (0.1 g, 0.2 mmol) in DCM (40 mL) was bubbled with HCl (gas) for 3 hours, then 40 mL NaOH solution (2 M) was added and the mixture was stirred for 2 hours. The resulting mixture was extracted with EtOAc (20 mL×3). The EtOAc layers were combined and dried, concentrated under reduce pressure to give a residue, which was purified by flash chromatography on $SiO_2$ (Hexane:EtOAc=1:2) to give desired compound (20 mg, yield 25%).

1 H NMR (300 MHz, DMSO): δ 1.10-1.19 (m, 2 H), 1.30-1.53 (m, 4 H), 2.11-2.45 (m, 4 H), 5.25 (s, 2 H), 7.15-7.28 (m, 2 H), 7.42-7.50 (m, 2 H), 7.60-7.72 (m, 1 H), 7.85-7.96 (m, 2 H), 9.21 (s, 1 H), 10.1 (s, 1 H). LCMS found 405 [M+H]$^+$, HPLC (254 nm, purity 98%).

Example 5

Synthesis of CC No. 5, N-(6-((2-aminophenyl)amino)-6-oxohexyl)-4-bromobenzamide

This compound was made by the procedure shown below.

(1) Synthesis of 4-bromobenzoyl chloride

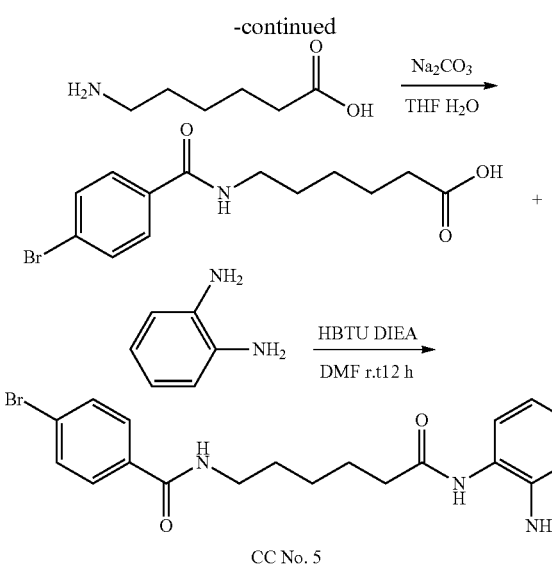

A mixture of 4-bromobenzoic acid (8 g, 39.8 mmoL) in SOCl$_2$ (80 mL) was stirred at 80° C. for 4 hours and then concentrated under reduce pressure. The resulting white solid was used directly for next step without further purification (8.5 g, yield 97.3%).

(2) Synthesis of 6-(4-bromobenzamido)hexanoic acid

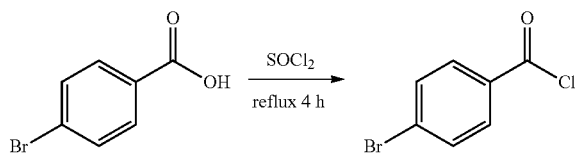 [SMILES: O=C(O)c1ccc(Br)cc1 ; "SOCl2" ; O=C(Cl)c1ccc(Br)cc1]

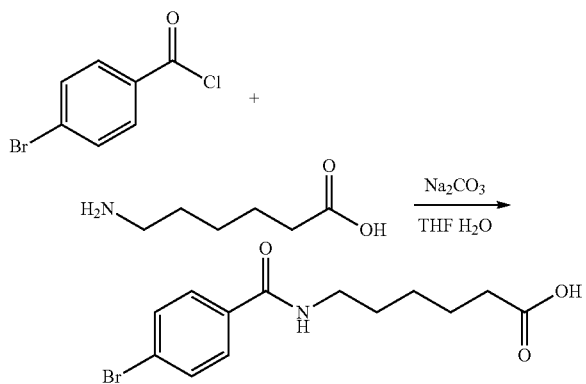

To a solution of 6-aminohexanoic acid (5.0 g, 38.7 mmol), Na$_2$CO$_3$ (4.1 g, 38.7 mmoL) in water (100 mL) was added drop-wise 4-bromobenzoyl chloride (8.5 g, 38.7 mmoL, dissolved in 80 mL THF) at 0° C. and stirred for 4 hours. The mixture was concentrated under reduced pressure. The pH value of the solution was adjusted to 1 by concentrated HCl. The resulting mixture was extracted by EtOAc (200 mL×3). The organic layers were combined and dried over Na$_2$SO$_4$, then concentrated to give the desired compound (7.5 g, yield 61.7%).

(3) Synthesis of N-(6-((2-aminophenyl)amino)-6-oxohexyl)-4-bromobenzamide

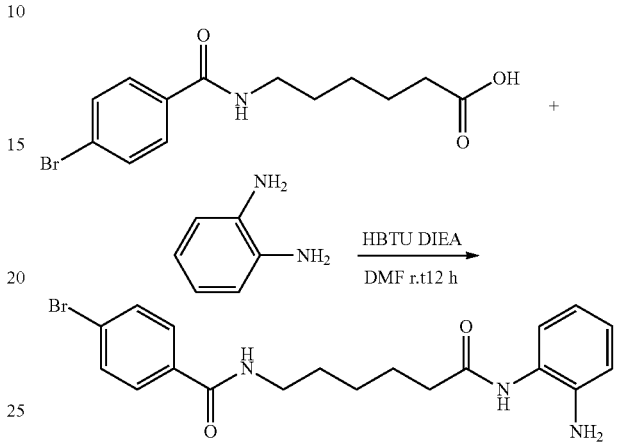

To a solution of 6-(4-bromolbenzamido)hexanoic acid (7.5 g, 23.9 mmol) in DMF (150 mL) was added benzene-1,2-diamine (10.3 g, 95.6 mmol), HBTU (9 g, 23.9 mmol), DIEA (16.7 mL, 95.6 mmol). The mixture was stirred at room temperature for 12 hours. The resulting mixture was poured into water and extracted by EtOAc (200 mL×3). The organic layers were combined and washed with saturated aqueous solution of Na$_2$CO$_3$, dried over Na$_2$SO$_4$ and then concentrated to give the crude product. The crude product was purified by flash chromatography SiO$_2$ (EtOAc:PE=1:1) to give the desired compound (6.4 g, yield 66.3%).

m.p.: 161.3-161.7° C., 1 H NMR (400 MHz, DMSO): δ 1.38-1.39 (m, 2 H), 1.55-1.66 (m, 4 H), 2.31-2.36 (m, 2 H), 3.24-3.28 (m, 2 H), 4.90 (s, 2 H), 6.52-6.57 (m, 1 H), 6.72-6.75 (m, 1 H), 6.88-6.93 (m, 1 H), 7.14-7.16 (m, 1 H), 7.67-7.70 (m, 2 H), 7.79-7.81 (m, 2 H), 8.55-8.57 (t, 1 H), 9.12 (s, 1 H). LCMS found 404 [M+H]+, HPLC (254 nm, purity 100%).

Example 6

Synthesis of CC No. 6, N$^1$-(2-aminophenyl)-N$^7$-(2-bromophenyl)heptanediamide

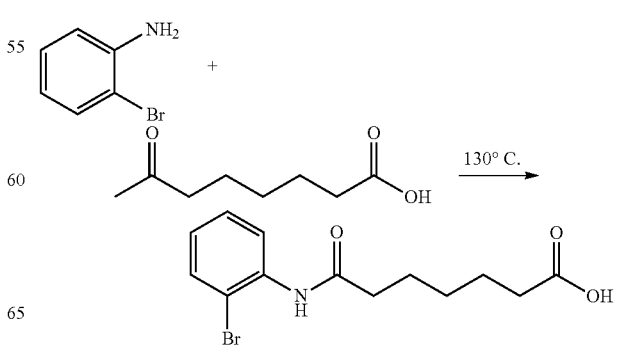

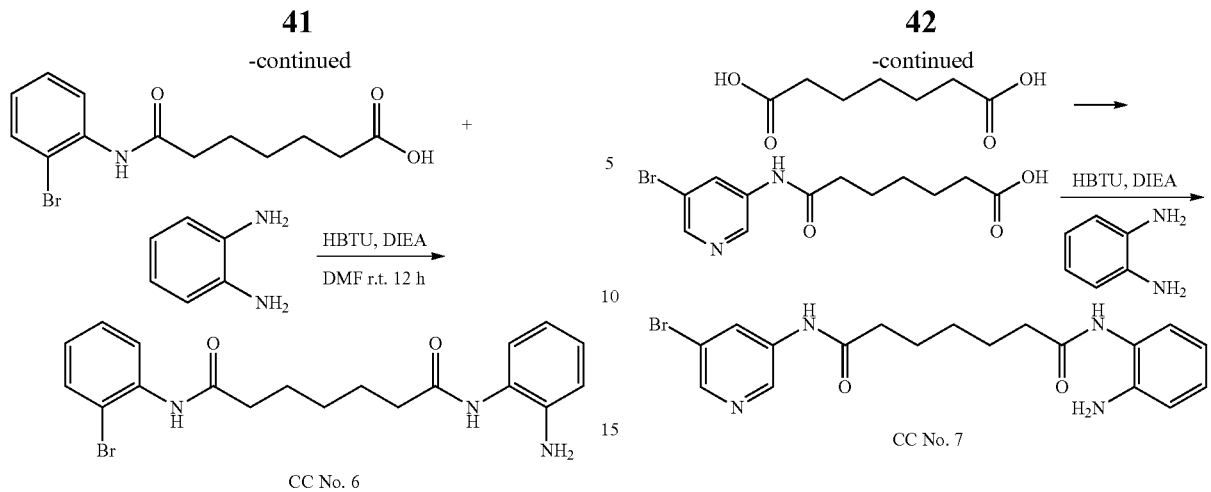

(1) Synthesis of 7-((2-bromophenyl)amino)-7-oxoheptanoic acid

The mixture of 2-Bromoaniline (317.5 g, 1.84 mol) and Pimelic acid (354.9 g, 2.21 mol) was heated and stirred at 130° C. for 8 h. After the reaction was completed, the solution was cooled to 50° C. Then the solution was added to NaOH solution (150 g NaOH in 3 L water). The mixture was filtered. And the concentrated HCl was added to the filtration until pH=1. The mixture was filtered to give the crude product as a yellow solid. The crude product was added to 3 L water. And NaOH was added to the mixture until pH=14. The mixture was filtered and the filtration was adjusted pH value to 1 by concentrated HCl. The mixture was filtered and given the product as pale white (yield 43.2%).

(2) Synthesis of $N^1$-(2-aminophenyl)-$N^7$-(2-bromophenyl)heptanediamide

To a solution of 7-((2-bromophenyl)amino)-7-oxoheptanoic acid (140 g, 0.45 mol) in DMSO (980 mL) was added CU (79.6 g, 0.49 mol). The solution was stirred at room temperature for 1 h. Then 1,2-diaminobenzene (361.3 g, 3.35 mol) was added and the solution was stirred at 35° C. for 2 h. After TLC showed the reaction was completed, 2 L water was added to the solution. The mixture was stirred at room temperature for 30 min. Then the mixture was filtered to give the crude product as a yellow solid. The crude product was recrystallization by methanol to give product as a white solid CC No. 6 (yield 72.1%, mp 160.3-161.0° C.).

1 H NMR (400 MHz, DMSO): δ 1.39-1.41 (m, 2 H), 1.62-1.66 (m, 4 H), 2.31-2.37 (m, 4 H), 4.79 (s, 2 H), 6.51-6.54 (m, 1 H), 6.70-6.72 (m, 1 H), 6.87-6.90 (m, 1 H), 7.11-7.17 (m, 2 H), 7.33-7.36 (m, 1 H), 7.56-7.58 (m, 1 H), 7.63-7.65 (m, 1 H), 9.06 (s, 1 H), 9.37 (s, 1 H). LCMS found 404.1 [M+H]+, HPLC (254 nm, purity 99%).

Example 7

Synthesis CC No. 7, N'-(2-aminophenyl)-$N^7$-(5-bromopyridin-3-yl) heptanediamide

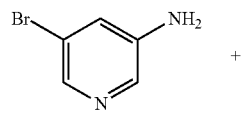

(1) Synthesis of 7-((5-bromopyridin-3-yl)amino)-7-oxoheptanoic acid

The mixture of 5-bromopyridin-3-amine (2.0 g, 11.6 mmol) and heptanedioic acid (2.22 g, 13.9 mmol) was heated and stirred at 130° C. for 8 h. After the reaction was completed, the solution was cooled to 50° C. and added to NaOH solution. The mixture was filtered. The filtration was extracted with EtOAc (50 mL×3) and concentrated HCl was added until pH=1. The solid was collected to give the product as a yellow solid 2.42 g (yield 66.2%).

(2) Synthesis of $N^1$-(2-aminophenyl)-$N^7$-(5-bromopyridin-3-yl)heptanediamide To a solution of 7-((5-bromopyridin-3-yl)amino)-7-oxoheptanoic acid (1.0 g, 3.2 mmol) in DMF (30 mL) was added HBTU (1.8 g, 4.7 mmol), DIEA (0.82 g, 6.3 mmol), 1,2-diaminobenzene (1.04 g, 9.6 mmol). The solution was stirred at 35° C. for 2 h. After TLC showed the reaction was completed, 50 mL water was added to the solution. The mixture was stirred at room temperature, for 30 min. Then the mixture was filtered to give the crude product as a yellow solid. The crude product was recrystallized by methanol to give product as a yellow solid (yield 55.9%).

m.p.: 129.9-130.1° C., $^1$H NMR (500 MHz, DMSO): δ 1.34-1.40 (m, 2 H), 1.60-1.67 (m, 4 H), 2.31-2.38 (m, 4 H), 4.79 (s, 2 H), 6.51-6.54 (m, 1H), 6.70-6.72 (m, 1 H), 6.87-6.90 (m, 1 H), 7.13-7.15 (m, 1 H), 8.36 (m, 1 H), 8.38-8.39 (m, 1 H), 8.64-8.65 (m, 1H), 9.05 (s, 1 H), 10.3 (s, 1 H). LCMS found 405 [M+H]+.

Example 8

Mammalian Two-Hybrid Assay Used to Determine the Inhibitory Effects of the Compounds on MEF2D and HDAC4 Protein Interactions Methods Detection of MEF2D and HDAC4 interactions. In this mammalian two-hybrid assay, HDAC4 and MEF2D proteins were used as representative members of their respective protein families because the protein-protein interactions involved in the recruitment of class IIa HDACs by MEF2 were highly conserved. Two separate DNA constructs were made with MEF2D fused with the GAL4 DNA binding domain (GAL4-MEF2D) and with the MEF2-binding motif of HDAC4 (AA 155-220) fused with the viral transactivator VP-16 (HDAC4-VP16) (FIG. 1). Human epithelial carcinoma cells (HeLa) were co-transfected with the two DNA constructs (GAL4-MEF2D and HDAC4-VP16) and a reporter plasmid (Gal4Luc). The DNA constructs resulted in expression of the GAL4-MEF2D and HDAC4-VP16 fusion proteins within the cell. MEF2D and HDAC4 protein interactions were detected as a result of the GAL4-MEF2D and HDAC4-VP16 protein complex binding a DNA promoter on the reporter plasmid (Gal4Luc) and driving cellular expression of a luciferase gene (FIG. 1). The measured luciferase protein signal was proportional to the amount of MEF2D and HDAC4 protein interactions occurring with the cell.

Figure 2:
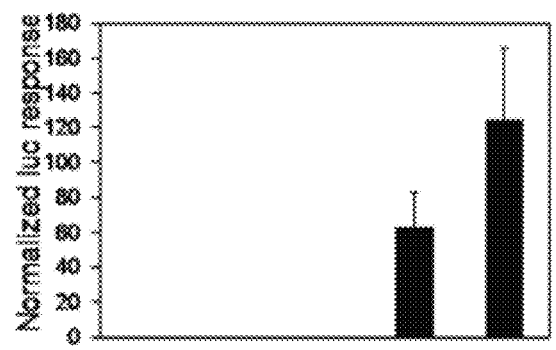
FIG. 2—A graph depicting the normalized luciferase response when HeLa cells were co-transfected with the Gal4Luc reporter plasmid either alone or with the GAL4-MEF2D construct only, with the HDAC4-VP16 construct only, with the GAL4-MEF2D and HDAC4-VP16 constructs together (producing a reporter signal), or with the positive control GAL4VP16 construct (producing a stronger reporter signal).

Co-expression of GAL4-MEF2 and HDAC4-VP16 DNA constructs produced a luciferase response comparable to that generated by the positive control GAL4-VP16 fusion (GAL4VP16) in HeLa cells (FIG. 2). The relatively stronger signal from the GAL4VP16 positive control construct was probably due to the fact that the activation domain of VP16 was covalently linked to GAL4, whereas in the mammalian two-hybrid assay it was recruited by protein-protein interactions between HDAC4 and MEF2 (FIG. 2). This assay permitted the detection of the interactions between HDAC4 and MEF2D with minimal interference from endogenous factors. The HDAC4 fragment lacked the catalytic domain so that the deacetylase activity was excluded from the assay.

Detection of inhibition of MEF2D and HDAC4 interactions. Next, the assay was used to test whether the compounds could disrupt the interactions between MEF2D and HDAC4. After co-expressing the GAL4-MEF2D and HDAC4-VP16 DNA constructs and reporter plasmid, the HeLa cells were treated with a test compound (10 μM) overnight. Cells transfected with the positive control GAL4VP16 fusion construct and reporter plasmid were also treated with the test compound (10 μM) overnight. As another control, DMSO was added (but kept below 0.2% V/V) to cells transfected with the positive GAL4VP16 fusion construct or the GAL4-MEF2D and HDAC4-VP16 DNA constructs. A luciferase assay was performed as described above according to the manufacturer's protocol (Promega). The luciferase response was normalized against the Renilla Luciferase as an internal control.

The relative activity and $IC_{50}$ calculations. The test compound, at a concentration of 10 μM, decreased the reporter signal driven by GAL4-MEF2D and HDAC4-VP16 protein complex by X fold, while the control solution, which was DMSO, also decreased the reporter signal by Y fold. The relative activity, I, was the ratio of former to later, i.e. X/Y, expressed in percentile. The relative activity for compounds showing the strongest inhibition was low compared with those compounds that showed little to no inhibition of MEF2D and HDAC4 interactions. The $IC_{50}$ was the concentration of the compounds when X/Y equals 50.

Results

The compounds were categorized into Groups A-D. Compounds in Group A had a relative activity between 0 and 22 (Table 2). The relative activity of Group B compounds was between 22 and 50 (Table 2). Compounds in Group C and Group D had relative activities between 50 and 100 and above 100, respectively (Table 2). Group A compounds were the most effective inhibitors of MEF2D and HDAC4.

TABLE 2

Inhibition of MEF2D/HDAC4 protein-protein interactions

| Compound Name | Structure | Relative Activity, I | $IC_{50}$ (μM) | Group** |
|---|---|---|---|---|
| CC1 | 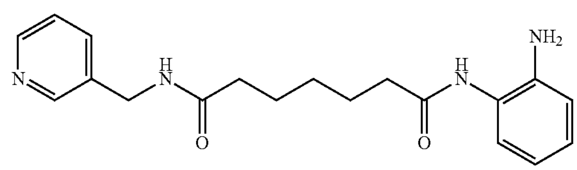 [SMILES: Nc1ccccc1NC(=O)CCCCCC(=O)NCc1cccnc1] | 79.2 | ND* | C |
| CC2 | 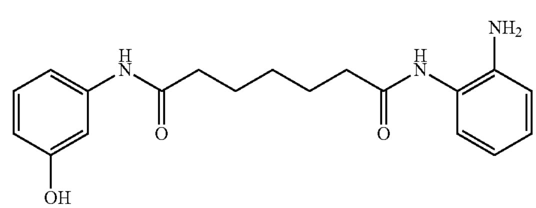 [SMILES: Nc1ccccc1NC(=O)CCCCCC(=O)Nc1cccc(O)c1] | 4.7 | 0.09 | A |
| CC3 | 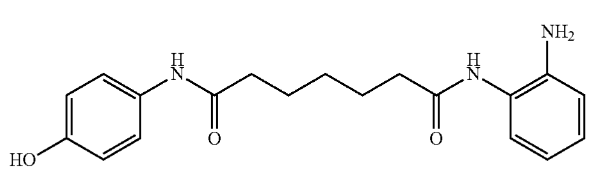 [SMILES: Nc1ccccc1NC(=O)CCCCCC(=O)Nc1ccc(O)cc1] | 5.4 | 0.10 | A |
| CC4 | 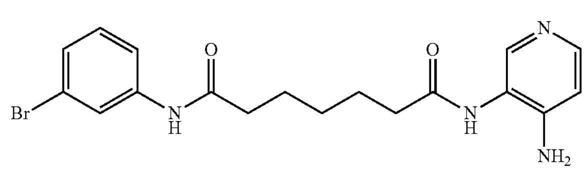 [SMILES: Nc1ccncc1NC(=O)CCCCCC(=O)Nc1cccc(Br)c1] | 79.5 | ND* | C |

TABLE 2-continued

Inhibition of MEF2D/HDAC4 protein-protein interactions

| Compound Name | Structure | Relative Activity, I | IC$_{50}$ (μM) | Group** |
|---|---|---|---|---|
| CC5 | (4-bromobenzamide linked via pentyl chain to 2-aminophenyl amide) | 3.6 | 0.07 | A |
| CC6 | (2-bromoanilide linked via hexyl chain to 2-aminoanilide) | 62.6 | ND* | C |
| CC7 | (5-bromopyridin-3-yl amide linked via pentyl chain to 2-aminophenyl amide) | 5.7 | 0.11 | A |

*ND: not detected.
**Group:
A (I < 22 included),
B (22 < I < 50 included),
C (50 < I < 100 included),
D (I > 100),
wherein I is relative activity.

The assay results showed that the test compounds were able to inhibit MEF2 and HDAC4 interactions. The inhibition was not dependent upon the compound binding to the HDAC4 active site because the active site of the HDAC4 protein was not expressed in the assay.

Unlike currently available HDAC inhibitors, the inhibitory results of the compounds in this specific assay demonstrated that they could specifically target and inhibit class IIa HDAC interactions with MEF2. The assay utilized a specific domain of HDAC4 (amino acids 155-220) that was unique only to class IIa HDACs. The significance of this result was that these compounds may be able to affect the development or progression of a disease by specifically regulating a specific class of HDACs (class IIa) without the adverse consequences of disrupting the essential functions of the entire HDAC protein family, such as HDACs in classes I, IIb, and IV.

The following Example demonstrates the significant potential of these compounds in controlling disease with an assay that showed that they can inhibit the growth of leukemia cells.

Example 9

Inhibition of Nalm-6 Leukemia Cell Growth

Method
Treatment of cells. Nalm-6 leukemia cells were grown to the logarithmic growth phase and seeded into 24-well plates. Plated cells were incubated at 37° C. in a 5% $CO_2$ humidified incubator for 24 hours and treated with various concentrations of compounds. Treated cells were further incubated for 72 hours and then were examined for cell proliferation. Cell proliferation was determined using the CellTiter-Glo Luminescence Cell Viability assay (Promega Corporation, Madison, Wis.) according to the manufacturer's protocol. The calculated inhibition rate was determined with the following formula: Inhibition rate (%)=(1−Luminescence of experimental group/Luminescence of control group)×100. The $10_{50}$ was the calculated concentration of a compound needed to inhibit half of the maximum cell growth (equivalent to cell growth in control group) based on the corresponding dose-response curve under the described experimental conditions.

Results
Inhibition of the growth of the Nalm-6 leukemia cell line. Table 3 displays the survival percentage of Nalm-6 leukemia cells that were treated with the compounds. These data were consistent with the results observed in the two-hybrid assay presented in Example 8. All of the Group A compounds consistently showed strong growth inhibition of the Nalm-6 leukemia cells. The cell growth inhibition for compounds CC1 and CC4 were comparable to the results in the two-hybrid assay showing a mild inhibitory effect in both assays. Surprisingly, compound CC6 of Group C showed a strong growth inhibition response comparable to the Group A compounds. Since CC6 showed a weaker inhibition of interactions between HDAC4 and MEF2, the strong growth inhibition of leukemia cells by CC6 was likely a result of CC6 inhibition of MEF2 interactions with other transcription co-factors rather than class IIa HDACs.

TABLE 3

Inhibition of Nalm-6 leukemia cell growth

| Compound Name | Nalm 6 IC$_{50}$ (μM) |
|---|---|
| CC1 | >10 |
| CC2 | 1.46 |
| CC3 | 2.61 |

TABLE 3-continued

Inhibition of Nalm-6 leukemia cell growth

| Compound Name | Nalm 6 IC$_{50}$ (µM) |
|---|---|
| CC4 | >10 |
| CC5 | 1.38 |
| CC6 | 2.05 |
| CC7 | 1.36 |

REFERENCES

The references, patents and published patent applications listed below, and all references cited in the specification above are hereby incorporated by reference in their entireties, as if fully set forth herein.
1. Physician's Desk Reference, 41st Ed., Publisher Edward R. Barnhart, N.J. (1987).
2. PCT/US93/0082948.
3. Remington: The Science and Practice of Pharmacy, 21st Edition, Univ. of Sciences in Philadelphia (USIP), Lippincott Williams & Wilkins, Philadelphia, Pa., 2005.
4. Wu, L., Smythe, A. M., Stinson, et. al. Multidrug-resistant Phenotype of Disease-oriented Panels of Human Tumor Cell Lines Used for Anticancer Drug Screening. (1992) Cancer Research 52: 3029-3034.
5. Bradner J E, West N, Grachan M L, Greenberg E F, Haggarty S J, Warnow T, Mazitschek R. Chemical phylogenetics of histone deacetylases. Nat. Chem. Biol. 2010; 6: 238-243.
6. Lu J, McKinsey T A, Zhang C L, Olson E N. Regulation of skeletal myogenesis by association of the MEF2 transcription factor with class II histone deacetylases. Mol. Cell. 2000; 6:233-244.
7. Wang A H, Yang X J. Histone deacetylase 4 possesses intrinsic nuclear import and export signals. Mol. Cell. Biol. 2001; 21:5992-6005.
8. Han A, He J, Wu Y, Liu J O, Chen L. Mechanism of recruitment of class II histone deacetylases by myocyte enhancer factor-2. J. Mol. Biol. 2005; 345:91-102.
9. Han A, Pan F, Stroud J C, Youn H D, Liu J O, Chen L. Sequence-specific recruitment of transcriptional co-repressor Cabin1 by myocyte enhancer factor-2. Nature. 2003; 422:730-734.
10. Jayathilaka, et al., Nucleic Acids Res. 2012 July; 40(12): 5378-5388.
11. Potthoff, M., and Olson, E. N. Development. 2007 December; 134 (23): 4131-4140.

What is claimed is:

1. A compound having a structure of

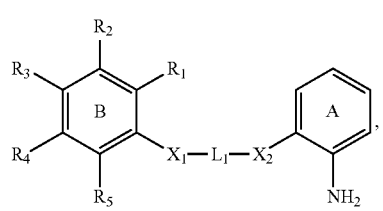

Structure I including pharmaceutically acceptable solvates, pharmaceutically acceptable prodrugs, pharmaceutically acceptable salts and pharmaceutically acceptable stereoisomers thereof, wherein:

A ring is a phenyl;
$R_1$, $R_3$, and $R_5$ are hydrogen;
$R_4$ is selected from the group consisting of halogen, alkyl, OH, haloalkyl, aryl, heteroaryl, aryl carbonyl, and amino;
$X_1$ and $X_2$ are independently selected from —NHC(=O)— or —C(=O)—NH—;
$L_1$ is —(CH$_2$)$_n$—, where n is 4, 5, 6, 7, or 8; and
$R_7$ is selected from the group consisting of alkyl group having 1-3 carbon atoms and methyl.

2. A compound having a structure of Structure IX:

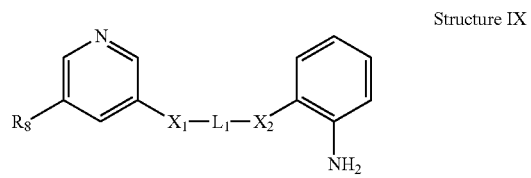

Structure IX including pharmaceutically acceptable solvates, pharmaceutically acceptable prodrugs, pharmaceutically acceptable salts and pharmaceutically acceptable stereoisomers thereof, wherein:

$X_1$ and $X_2$ are independently selected from —NHC(=O)— or —C(=O)—NH—;
$L_1$ is —(CH$_2$)$_n$—, where n is 4, 5, 6, 7, or 8; and
$R_8$ is selected from the group consisting of halogen, F, Cl, Br, I, alkyl, CH$_3$, C$_2$H$_5$, OH, haloalkyl, CF$_3$, aryl, phenyl, heteroaryl, pyridyl, aryl carbonyl, phenylcarbonyl, amino, NH$_2$.

3. The compound according to claim 2, selected from the group consisting of

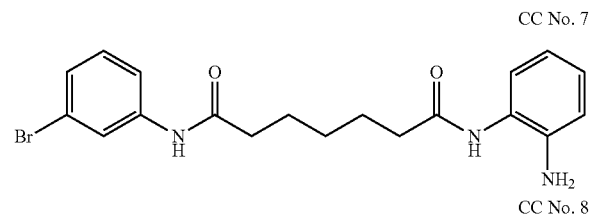

CC No. 7

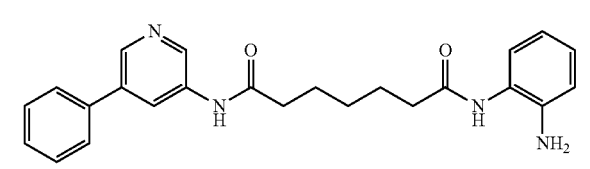

CC No. 8

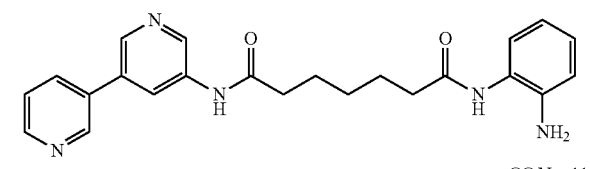

CC No. 9

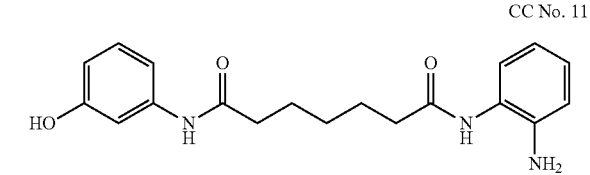

CC No. 11

CC No. 12
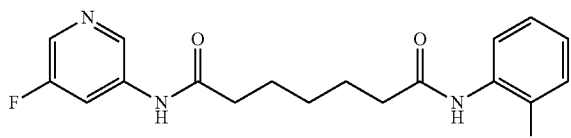
CC No. 13
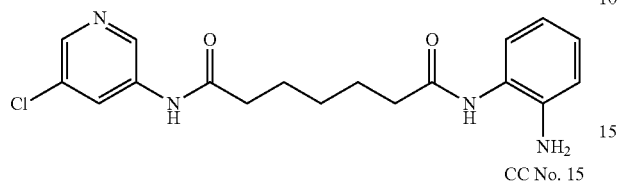
CC No. 15
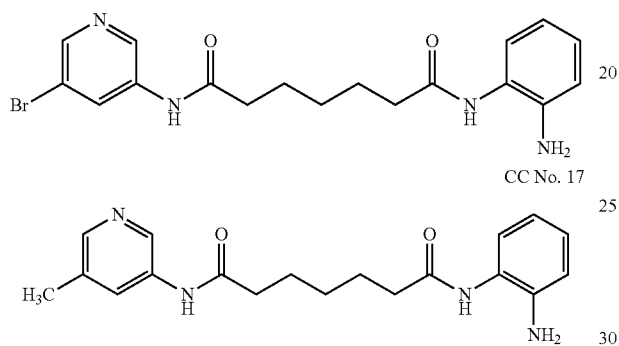
CC No. 17
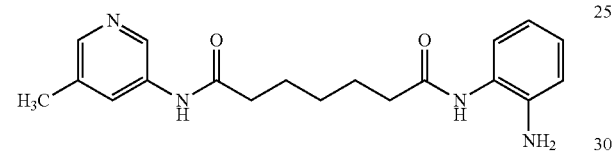
CC No. 18
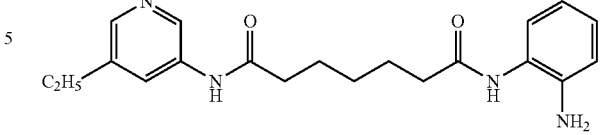
CC No. 19
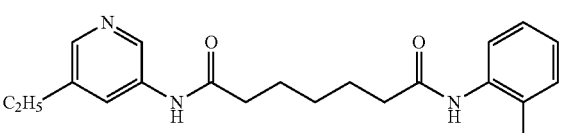
and
CC No. 20
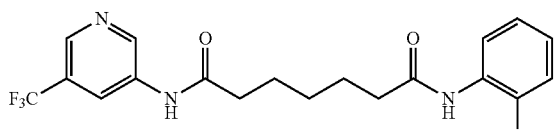
* * * * *